United States Patent [19]

Van Buskirk et al.

[11] Patent Number: 5,062,304
[45] Date of Patent: Nov. 5, 1991

[54] URINE COLLECTION MONITOR WITH TEMPERATURE SENSING

[75] Inventors: Robert S. Van Buskirk, Danville; Robert R. Clappier, Los Altos, both of Calif.

[73] Assignee: Endotherapeutics, Menlo Park, Calif.

[21] Appl. No.: 351,733

[22] Filed: May 12, 1989

[51] Int. Cl.$^5$ .............................................. G01F 1/00
[52] U.S. Cl. ...................................... 73/861; 4/114.2; 4/114.1; 128/760; 73/223
[58] Field of Search ................ 4/144.1, 144.2; 73/223, 73/304 C, 861, 198; 128/760, 761, 771

[56] References Cited

U.S. PATENT DOCUMENTS

| | | |
|---|---|---|
| 3,729,994 | 5/1973 | Klug . |
| 3,930,411 | 1/1976 | Beeker et al. . |
| 4,051,431 | 9/1977 | Wurster et al. . |
| 4,408,905 | 10/1983 | Ehrenkronz ................ 128/761 X |
| 4,448,207 | 5/1984 | Parrish ................ 128/771 |
| 4,458,539 | 7/1984 | Bilstad et al. ................ 73/861 |
| 4,554,687 | 1/1985 | Carter et al. ................ 128/760 X |
| 4,557,274 | 12/1985 | Cawood ................ 128/760 |
| 4,564,229 | 1/1986 | Ehrenkranz ................ 128/771 X |
| 4,683,748 | 8/1987 | Carter ................ 128/760 X |

OTHER PUBLICATIONS

Drach et al., (1976) *J. Urology* 115:175-179.
Siroky et al., (1980) *J. Urology*, 123:208-210.
Susset et al., (1973), *J. Urology* 109:874-878.
Corlett, Jr. et al., (1979) *J. Urology* 122:512-514.

*Primary Examiner*—Herbert Goldstein
*Attorney, Agent, or Firm*—Irell & Manella

[57] ABSTRACT

An apparatus and method for flow and temperature analysis during collection of a urine sample, and for simultaneously maintaining the urine sample sterile. A disposable vessel for collecting the urine is mounted on a commode adapter, and includes a variable capacitor, with a capacitance value which varies with the amount of urine in the vessel. The variable capacitor forms a part of a capacitance bridge. A microprocessor controlled by a clock is used to periodically sample the varying capacitance value as fluid flows into the vessel, and thereby determine the flow rates of the fluid. A tube is provided which communicates with the interior of the vessel for drawing off a sterile sample of the urine for laboratory analysis, and a drain is provided which is operable without contacting the urine. Temperature sensing means are provided for detecting the temperature of the fluid as a function of time, comprising a thermistor or an infrared optical sensor.

24 Claims, 15 Drawing Sheets

URINE COLLECTION MONITOR WITH TEMPERATURE SENSING

BACKGROUND OF THE INVENTION

The present invention relates to a method and an apparatus for determining temperatures and flow rates of urine during micturition and for determining other variables, and for obtaining a urine sample for clinical laboratory analysis.

Measurement of urinary flow rates (uroflowmetry) during micturition is an important technique of evaluating lower urinary tract dysfunction. Average flow rates and the peak flow rate, along with the patterns of changing flow rates during the micturition event allow physicians to identify conditions of outflow obstruction and differentiate between anatomic and neurologic disease.

The simplest form of uroflowmetry is observation of the urine stream by a trained physician. A simple and more quantifying technique is timing the voiding of a patient while collecting the urine into a calibrated container, thereby allowing average flow rate to be calculated. Other devices allow peak flow rate to be estimated by collecting urine into chambers of varying sizes in a device, with the filling of the chambers dependent upon flow rates. Observation of urination, however, is embarrassing to many patients, and many cannot void or do not void normally under such conditions. Furthermore, observation, timed voiding, and peak flow measurement alone give only partial information about how the patient urinates.

Electro-mechanical devices have been devised to make a recording of urine flow rates during micturition. Many technologies have been used to make the measurement. Measurement by weight is a common technique. Weight represents volume, and change in weight over time represents flow rate. Other technologies include micro-turbines in which the urine flowing through a tube acts upon a small fan blade, the rotation of which is proportional to urine flow rate, with the rotation being measured optically. Another technique employs a DC motor with a blade rotating at a fixed speed. The urine acts upon the blade to impede its rotation causing the motor to draw more current to rotate the blade at a fixed speed. The change in current draw is then measured and reflects flow rate. Other techniques reported include measurement of the electrolytic properties of urine, measurement of the cooling effect of the flow of urine on a heated electrode, and occlusion of a $CO_2$ valve by the urine stream. Further, in the past a capacitor has been used to measure volume in a cylinder with change in volume representing flow rate. However, such a device has not been acceptable in practice because of the errors which result in certain portions of the data generated.

With the exception of the weight transducer method, all the other techniques require the urine to come into contact with the sensor mechanism. This has several shortcomings. First, the sensors must endure repeated exposure to urine, which is corrosive and damaging to the sensors. Cleaning is of utmost importance to maintain reliable performance of the sensor. Cleaning is also important in that infected urine may remain in or on the mechanism, allowing bacteria to grow and exposing other patients to disease. Further, since urine from several patients comes into contact with the sensor mechanism, the urine cannot be used reliably for clinical chemical and microbiological analysis. On a practical basis, the sensor systems cannot be cleaned adequately to provide the level of cleanliness required for such urinalysis.

While the urine does not directly contact weight-type sensors, similar problems exist. Urine is collected into a vessel which rests on the weight sensor. The sensor must be isolated from patient contact, and the urine must be directed into the collector from a standard size and height channel such that the weight measurement is not changed by the kinetic forces of the urine stream. Therefore a weight-type apparatus must provide a means of directing the urine into the collection cup. Since urine contacts this portion of the apparatus (generally a large funnel), this system obviates the use of the voided urine for additional laboratory tests.

Patients requiring both urinalysis test and urine flow rate measurement now must void twice during the visit to the physician's office or clinic. This presents a practical problem, and in some cases patients try to hydrate quickly by drinking excessive amounts of fluid. This can lead to short-term metabolic imbalances which can distort the results of urinalysis. Many patients requiring the urine flow test also require urinalysis. Obstruction and infection are frequently concurrent and may have causal relationships. Outflow obstruction can cause high pressure in the bladder during micturition resulting in reflux of urine into the kidneys. This may result in impaired kidney function which is measured through chemical urinalysis.

Current alternatives to direct witnessing include: (1) temperature measurement of the sample after voiding as a test of whether it was freshly voided; (2) aural witnessing by an individual outside a commode stall or bathroom; (3) chemical analysis of the urine for pH and other characteristics; (4) requiring the subject to undress before entering the bathroom; (5) removal of faucets from the bathroom so the subject cannot dilute the sample with water; and (6) putting bluing agents in the toilet to prevent dilution with toilet water. None of these approaches is entirely satisfactory, however, and there is therefore a need for a system which eliminates such complicated, labor-intensive and unreliable steps.

Employment related and forensic drug testing of urine samples has increased greatly in recent years. However, a certain amount of fraud has occurred in the provision of samples. Organizations requiring the tests feel that in many instances the validity of the testing programs has been compromised. In order to ensure that samples are genuine and unadulterated, direct witnessing of the subject's urination is often required. This requirement causes a great deal of humiliation and embarrassment for many subjects. In addition, much of the collection is done in industrial medical clinics or other health-care institutions where the professional medical staff members are asked to witness the urination. Many find this inconsistent with their training, professional objectives and personal standards. Therefore, there is a need for an alternative to human witnessing as a means for ensuring that urine sample was freshly voided by the subject.

There is also a need for a system which provides a consistent, objective technique for collecting the sample, and for ensuring its validity. Protocols for ensuring authenticity vary from collection site to collection site, and may vary from shift to shift at a single collection site, because of the unwillingness of staff members to watch urination. In addition, any action taken with an individual being tested which even implies an attempt to provide a fraudulent sample may expose a testing agency to liability for uneven or unfair treatment. There is thus a need for a testing program with an automated, objective collection witnessing protocol, in order to reduce the potential for human error and uneven treatment.

SUMMARY OF THE INVENTION

The present invention provides a method and apparatus for verification of urine samples by temperature sensing coupled with flow analysis during collection of a urine sample, and for simultaneously maintaining the urine sample sterile for use in clinical and microbiological analysis. A collector assembly adapted to fit a standard commode is used and includes a fold-out liner covering the entire target area for capturing the urine stream during voiding. A variable capacitor is included in the collector assembly, which has a capacitance value which varies with the amount of fluid in the collector assembly. The variable capacitor is attached to a capacitance bridge, and the change in capacitance is provided as a voltage to a microprocessor for determining flow rates and other, related variables. A tube is provided for aspirating a urine sample from the collector for urinalysis, so that the sample is not handled by a person. The collector assembly also includes a drain mechanism allowing the unwanted urine to be drained into the commode without handling the assembly itself and protecting the operator of the apparatus from contact with the urine. The collector assembly is provided as a single unit for easy disposal when a given sample has been taken.

The variable capacitor has air acting as a dielectric, so that as the collector assembly fills with fluid, the capacitance changes.

The method of the invention involves determining a potential difference between two points in the capacitance bridge, with the potential difference relating to the changing capacitance value. This potential difference is processed for input into a microprocessor, which samples the processed potential difference periodically, thus determining the flow rate. Other variables which are determined are the peak flow rate, average flow rate and total time of micturition. A printer is connected to the microprocessor for outputting the flow versus time results, and a control panel is provided for either interface.

In a preferred embodiment of the invention, the system of the invention makes two independent sets of time-critical measurements on the voiding event. The first is a measurement of flow rate versus time, as discussed above, and the second is that of temperature versus time. These measurements are displayed or printed simultaneously as a function of time, and it is an object of the present invention to thereby provide a means of detecting non-genuine urine samples.

The temperature sensing in the preferred embodiment is carried out over several minutes, and measures the temperature decay rate relative to known standard data.

The present invention ensures that a valid urine sample has been provided by making two independent sets of time-critical measurements on the voiding event. The first is the measurement of urine flow versus time, and the second is that of temperature versus time. Together, these measurements make it extremely difficult to provide a nongenuine urine sample without detection.

In the embodiment of the invention which tracks temperature, as with the first embodiment discussed above, a single-use bucket and sensor are utilized, and a thermistor or other suitable low cost temperature measuring device is added to the bucket. The electronics are enhanced to include a resistive bridge to produce an appropriate electrical signal from the temperature measuring device. The output of the bridge is fed into a DC amplifier whose gain is set to provide a signal of an appropriate amplitude. In this case a standard analog-to-digital converter preceded by an analog switch or multiplexer is used to convert the information into a form suitable for the microprocessor. The room temperature is measured by a permanent internal temperature measuring device and its associated circuitry.

In some embodiments, the circuitry of the invention includes an astable multivibrator that uses a variable capacitor in the sensor to determine its operating frequency is used to measure the urine flow. The urine temperature and the reference temperature are also determined using astable multivibrators. For these measurements the astable multivibrators utilize fixed capacitors and use the changing resistance of the temperature sensor to determine the output frequency. The outputs of these three circuits are frequencies that can be processed directly by the microprocessor. The software of the invention is adapted in this case to process the temperature information, and this is plotted along with the urine flow data as a function of time.

In addition, the software must compare the urine flow data and the temperature data to normal patterns stored in program memory to determine whether the sample was normally voided. Since the variation of the detected urine temperature is influenced by the room temperature at the time of voiding, the computer is adapted to measure the room temperature and modify the expected temperature patterns accordingly.

DESCRIPTION OF THE PREFERRED EMBODIMENTS

Figure 1:
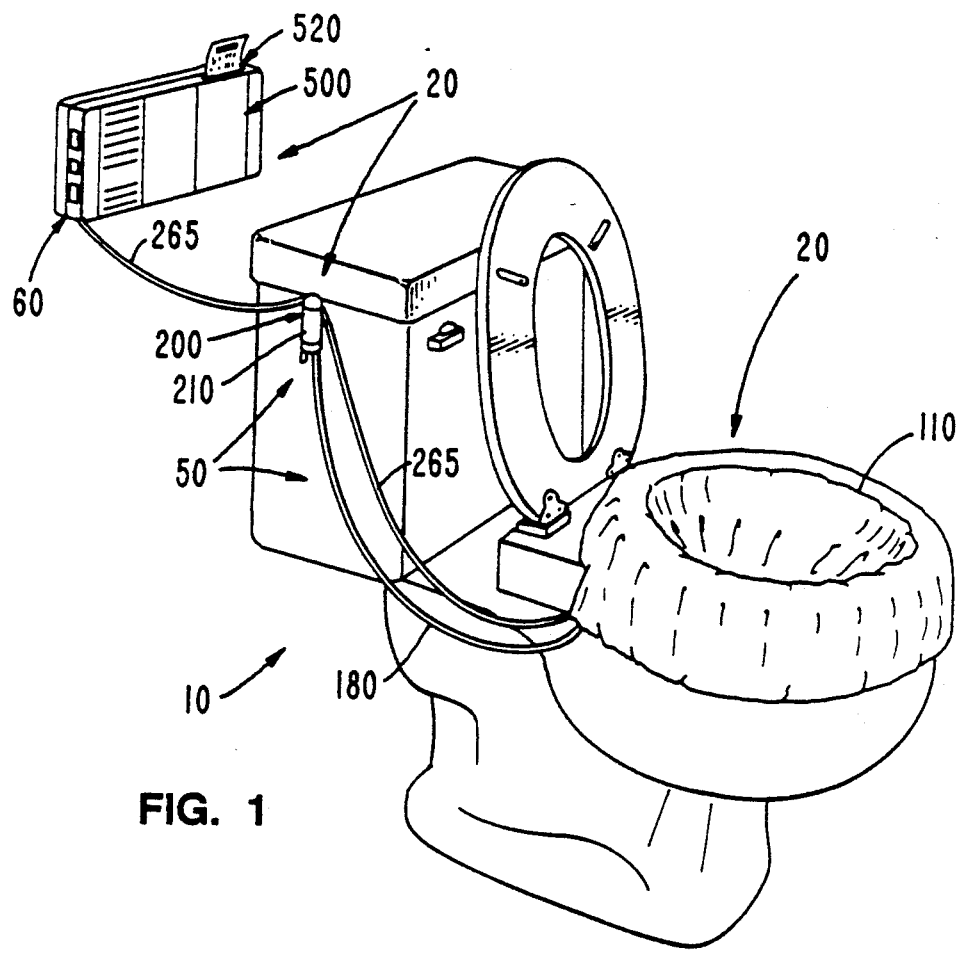
FIG. 1 is a perspective view of a commode utilizing the invention.
Figure 2:
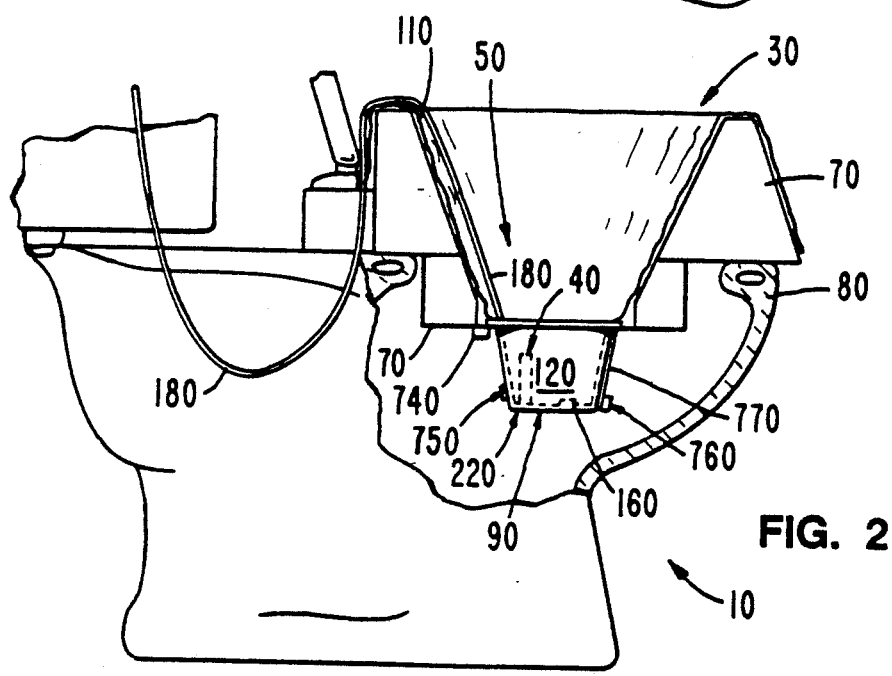
FIG. 2 is an elevation, partly in section, of a portion of the commode of FIG. 1.

FIGS. 1 and 2 show a typical toilet or commode 10 in connection with which the method and apparatus of the invention are used. The urine collection monitor 20 includes a urine collection system 30, a sensor 40, a urine sampling system 50, and an electronics module 60. The urine collection system 30 includes a commode adaptor 70 which is configured to fit over a standard toilet bowl 80. The adaptor 70 is a reusable item which may be left in place on the bowl 80. The collection system 30 also includes a vessel 90, which is basically bucket-shaped, and has a rim 100 (shown in FIG. 3) to which a liner 110 is attached in a fluid-sealing fashion. The rim 100 has a lip 105 for supporting the vessel 90 when it is inserted into the adaptor 70, which is preferably configured to the outside shape thereof.

Figure 3:
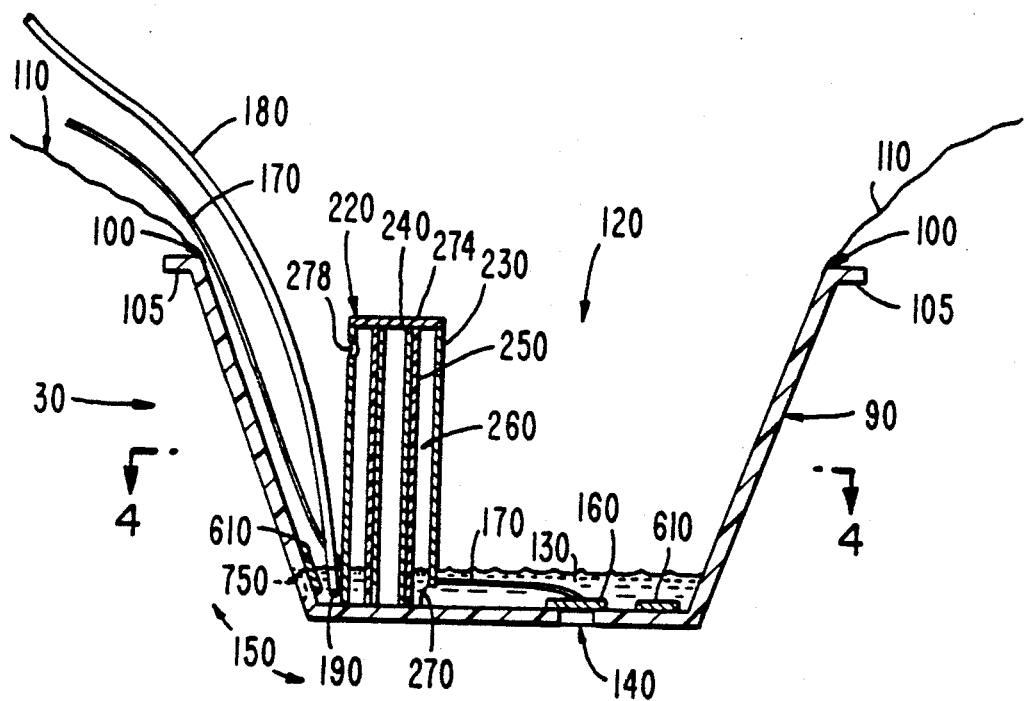
FIG. 3 is an enlarged view of a portion of FIG. 2.

Referring to FIGS. 2 and 3, the vessel 90 has a interior 120 in which a fluid 130, such as a patient's urine, is collected during micturition. (As will be apparent in the course of the following discussion, the principles of the invention are not confined to the specific application of uroflowmetry.) A drain is provided, comprising an aperture 140 which provides fluid communication between the interior 120 and an exterior 150 of the vessel 90. A plug 160 is provided for sealing the aperture 140, and a cord 170 or other means of pulling the plug 160 is provided. The cord 170 has one end attached to the plug 160, and the other end extending to the exterior of the urine collection system 30, so that when a sufficient sample has been collected and the necessary measurements have been taken, the plug 160 may be pulled opened as shown in FIG. 2 so that the urine flows out of the aperture 140 and into the commode 10, in order to dispose of the unwanted portion of the urine.

The plug 160 may comprise a piece of tape configured to seal the aperture 140, and the pulling means 170 may include a piece of tape with an end thereof attached to the plug 160, such that pulling of the pulling means 170 will shear or rupture the plug 160, allowing for draining of the fluid 130.

The use of the present device with its commode adaptor 70 allows the patient to void in a bathroom, rather than in a special apparatus set up in an examination room. This has the advantage of reducing deleterious psychological affects which may cause the patient to void in an abnormal fashion.

The urine sampling system 50 includes a conduit or tube 180 with one end having an opening 190 in communication with the interior 120 of the vessel 90, preferably near the bottom of the vessel. The other end of the tube 180 is connected to a means for drawing a sample from the interior 120 of the vessel 90, such as an evacuating device 200 of a type known in the art, which may be the VACUTAINER ™ evacuated test tube device produced by Beckton Dickinson and Co. of Rutherford, N.J., which includes a pre-evacuated receptacle 210. The tube 180 is connected by the user of the system to the receptacle 210, and has a seal adjacent thereto. The device 200 includes a needle (not separately shown) for puncturing the seal of the tube 180. Thus, when the patient has voided, the user of the monitor 20 punctures the seal, and the vacuum in the device 200 draws a sample of urine 130 from the interior 120 through the tube 180 into the receptacle 210. The receptacle 210 is then removed from the device and taken to a laboratory for urinalysis. Other means of drawing a sample may of course be utilized.

Since a urine sample may be aspirated through the conduit 180 without being handled by the physician, nurse or other operator of the device, the operator never needs to come in contact with urine, which may be infected. Similarly, the operator is protected from contacting the urine by means of the cord 170 which is utilized to drain the vessel 90 from a point remote therefrom, again preventing unwanted contact with potentially infected urine. It will also be appreciated that the vessel 90 and lining 110 shield the patient from the commode adaptor 70 and the commode 10 itself, thus protecting patients from possible contamination from earlier uses by other patients.

Figure 4:
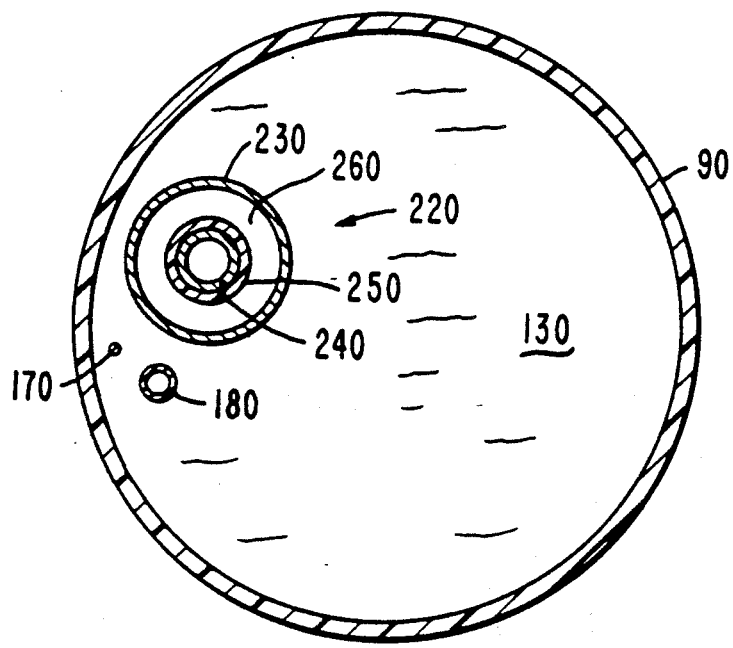
FIG. 4 is a view taken along line 4—4 of FIG. 3.

As shown in FIGS. 3 and 4, carried in the interior 120 of the vessel 90 is a variable capacitor 220 having a first electrode 230, a second electrode 240, a first dielectric 250 disposed around said second dielectric 240, and an air space 260 between the first electrode and the first dielectric, with the air space 260 acting as a second dielectric.

The first and second electrodes 230 and 240 and the first dielectric 250 are in this embodiment disposed in the interior 120 of the vessel 90. The first electrode 230 is configured as shown in FIG. 3 so as to allow communication of the fluid 130 with the air space 260, such as by including an aperture 270. Thus, as the vessel 90 is filled, urine 130 displaces air in the air space 260, thereby altering the capacitance value of the capacitor 220.

The top of the variable capacitor 220 may be open, in order to allow air present in the air space 260 to escape as it is displaced by incoming fluid. Otherwise, there would be resistance to the incoming flow, and possible turbulence due to bubbling as the air escapes past the fluid 130 at the bottom of the variable capacitor 220. Alternatively, in the preferred embodiment a cap 274 is provided atop the variable capacitor 220 to prevent splashed fluid or other materials from entering the air space 260 except through the aperture 270. In this embodiment, a second aperture 278 is provided in the electrode 230, to allow air to escape the air space 260, which would otherwise be inhibited by the cap 274.

Figure 5:
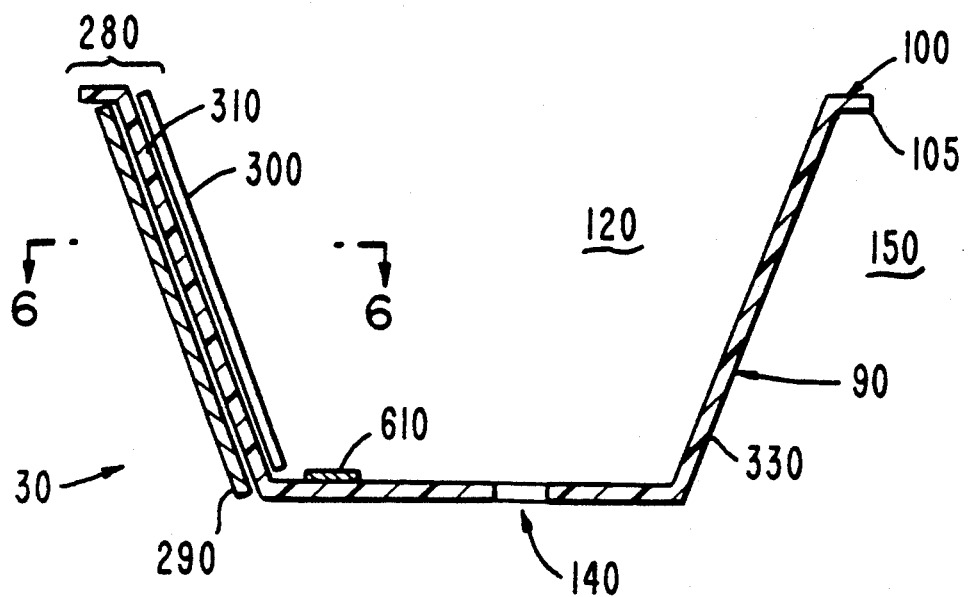
FIG. 5 is a view similar to FIG. 3, showing an alternative embodiment of the variable capacitor of the invention.
Figure 6:
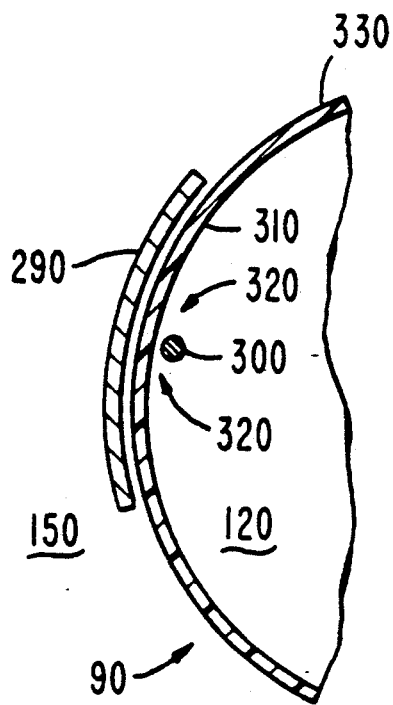
FIG. 6 is a view taken along line 6—6 of FIG. 5.

An alternative embodiment of the invention utilizes a variable capacitor 280 as shown in FIGS. 5 and 6. The capacitor 280 includes a first electrode 290, a second electrode 300, a first dielectric 310, and an air space 320 comprising a second dielectric of the capacitor 280. In this embodiment, the first dielectric 310 comprises a portion of a wall 330 of the vessel 90 defining the interior 120 and the exterior 150 of the vessel. The first electrode 290 is thus disposed adjacent the first dielectric 310 at the exterior 150 of the vessel 90. Urine 130 is therefore prevented from contacting the first electrode 290. In both embodiments of the variable capacitor (220 and 280), the electrodes may be made of brass, aluminum, or other conductors.

The second electrode 300 of the capacitor 280 may simply be a length of wire or a strip of conductor in tape form adhered to the inside of the vessel 90, and may or may not be electrically insulated from the fluid 130. The capacitor 280 exhibits relative independence of resistivity of the fluid, and therefore is relatively independent of the type of fluid which acts to vary the capacitance value thereof.

In the embodiments of FIGS. 3-4, the vessel 90, the variable capacitor 220, the liner 110, the plug 160, the cord 170, and the tube 180 comprise a single disposable unit. Thus, when one patient has used the collection system 30, and the appropriate data have been taken and a sample has been obtained, the plug 160 is pulled as described above, and then the tube 180 is detached from the receptacle 210, and the tube 180, the cord 170 and the liner 110 are stuffed into the interior 120 of the vessel 90 and the entire system 30 may be disposed of. Similarly, in the embodiment of FIGS. 5-6, the vessel 90, the lining 110, the second electrode 300, the cord 170 and the tube 180 comprise a single unit which may be disposed of once it is used. In the embodiment of FIGS. 5-6, the first electrode 290 may be either made a fixed part of the unit described above (such as a conductor in tape form or otherwise adhered to the vessel 90)—and therefore would be disposed of along with the vessel—or the first electrode 290 may alternatively be attached to the commode adaptor 70, depending therefrom for alignment with the wall 330 of the vessel 90 when it is placed in the commode adaptor 70 as in FIG. 2. The latter embodiment has the advantage of economy, since the first electrode 290 would be utilized repeatedly.

Figure 7:
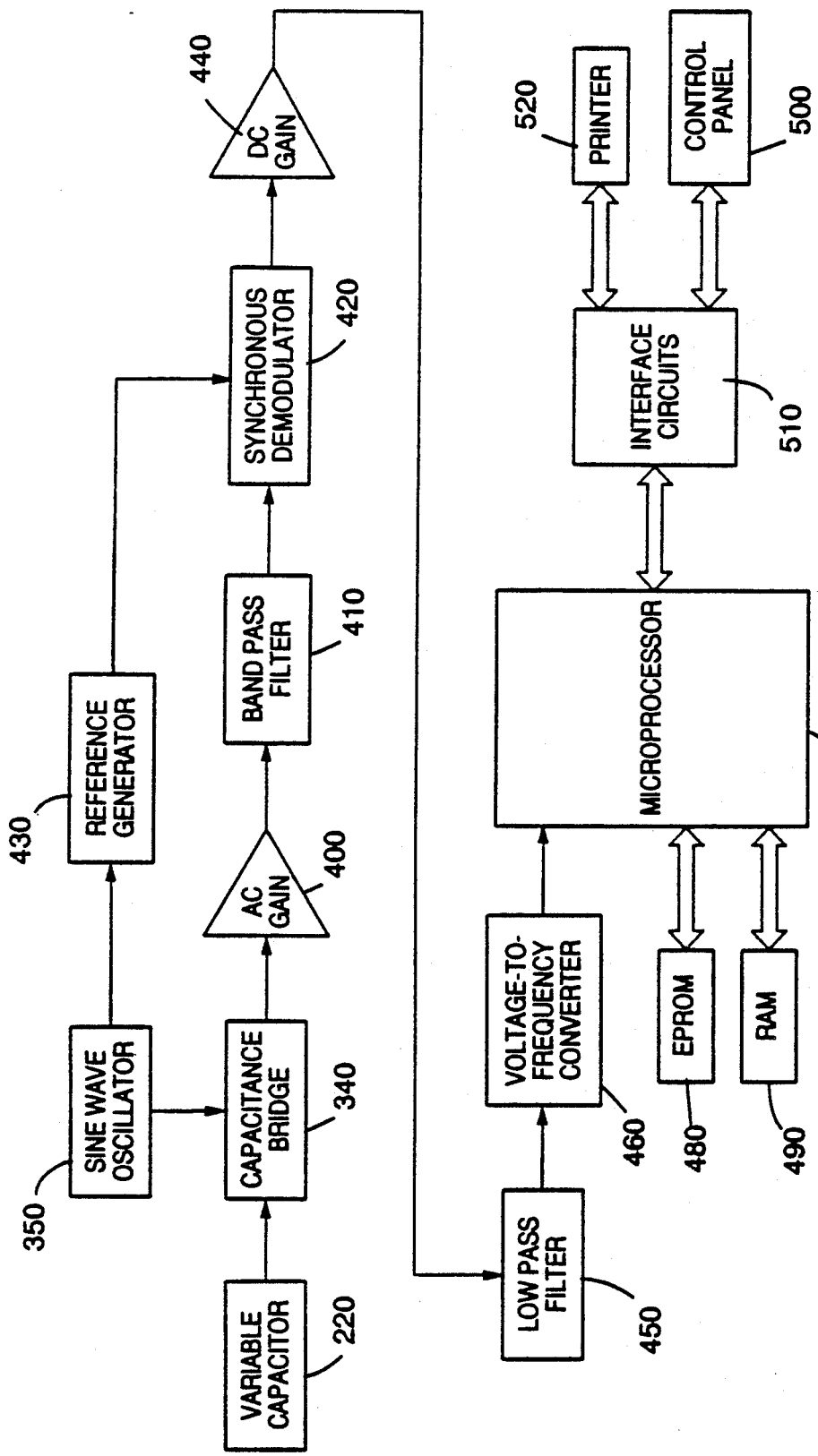
FIG. 7 is a block diagram of the processing circuitry of the invention.
Figure 8:
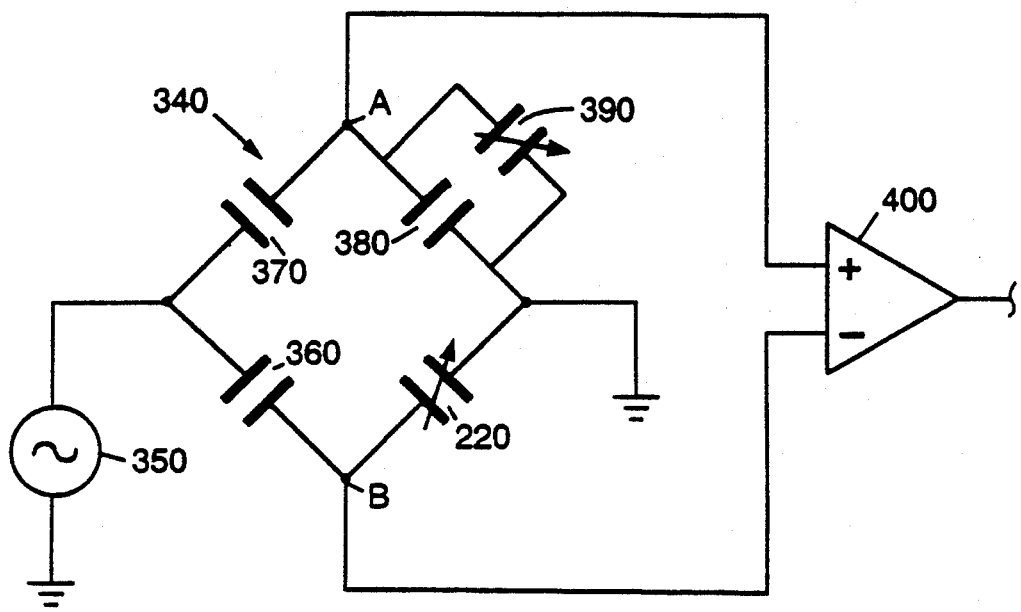
FIG. 8 is a schematic diagram of a capacitance bridge used in conjunction with the circuitry of FIG. 7.

The electrodes 230 and 240 of the variable capacitor 220 are electrically connected to a capacitance bridge circuit 340, as represented in FIGS. 7 and 8. This is done automatically when the user places the vessel 90 into the commode adapter 70, with both the vessel 90 and adaptor 70 being provided with contacts (not shown), so that when the vessel 90 is in place, the proper connections are made. A coaxial cable 265 (see FIG. 1) is provided for connecting the capacitor 220 to the module 60. In the course of the following discussion, any reference to the capacitor 220 may equivalently refer to the capacitor 280 or other variable capacitor configurations which would operate under the same principle.

All of the components shown in the block diagram of FIG. 7 are preferably carried by the electronics module 60, except for the variable capacitor 220. However, any desired portion of the circuitry may alternatively be carried by the commode adaptor 70.

A sine wave is provided by an oscillator 350 to the capacitance bridge 340, which includes, in addition to the variable capacitor 220, fixed capacitors 360, 370 and 380. When the capacitance values of the capacitors 220, 360, 370 and 380 are all equal, the potential difference between a first point A and a second point B of the circuit is zero. A differential operational amplifier 400 is connected to points A and B. Thus, when the capacitance values of the capacitors 220, 360, 370 and 380 are equal, no potential difference appears at the amplifier 400, which therefore has a zero output. (In the preferred embodiment, for practical reasons discussed below a small imbalance to the capacitance bridge 340 is deliberately provided by a trim capacitor 390, so that at least a small positive voltage always appears at the input to the amplifier 400.)

When fluid begins to fill the vessel 90, the capacitance of the variable capacitor 220 changes, thereby unbalancing the capacitance bridge 340, causing an increased potential difference between points A and B to appear at the amplifier 400. This potential is directly related to the amount of fluid in the vessel 90—and indeed is substantially proportional thereto—and thereby provides a means for measuring the same.

The output of the amplifier 400 is input to a band pass filter 410, which in the preferred embodiment passes frequencies frequencies in the range of about 500 Hz to 50 kHz, and minimizes any phase shift at the center frequency of approximately 5 kHz. This filter 410 operates to filter out line noise, radio frequency interference, and other high frequency noise, which may emanate from sources external to the monitor 20, or may emanate from other components of the monitor itself.

The signal, after filtering in the band pass filter 410, is input to a synchronous demodulator 420, which also has as an input an output from a reference generator 430 which is in turn driven by the sine wave oscillator 350. The synchronous demodulator 420 effectively rectifies the signal input thereto, obtaining a DC equivalent of the AC sine wave from the filter 410. As the vessel 90 fills, this signal grows in amplitude. The demodulator converts the input signal without significant phase shift, and with fast transitions.

Figure 10:
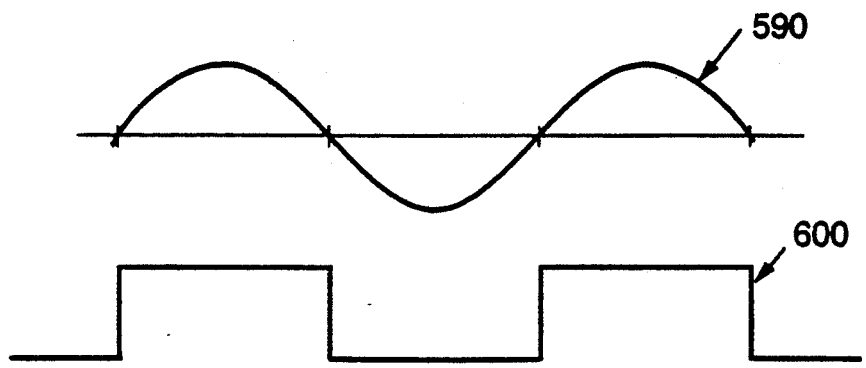
FIG. 10 is a diagram of the input and output to a reference generator utilized in the invention.

This demodulator 420 typically requires a square wave input from the reference generator 430. For this purpose, the reference generator 430 amplifies the signal from the oscillator 350, forming very steep transitions. Thus, if the signal is centered on zero volts, these steep transitions will occur around the zero crossings of the wave. An example of the intended conversion is shown in FIG. 10, with the waveform 590 representing an idealized input to the reference generator 430, and the waveform 600 representing the idealized output therefrom. In the preferred embodiment of this invention, the signal is actually centered on a positive voltage, with the minimum voltage being approximately zero; the demodulator functions equivalently for such a signal as for a signal centered on zero volts.

The reference generator 430 may use a Schmitt trigger, which actually detects points on the signal obtained from the oscillator 350 which are adjacent, but no quite at, the zero crossings. The output of the generator 230 is an approximately 5 kHz wave in phase with the sine wave input thereto. The generator 430 could also be used to generate a signal 180° out of phase with its input for use by the synchronous demodulator, if desired, so along as the zero crossings of the signal match up.

Figure 9:
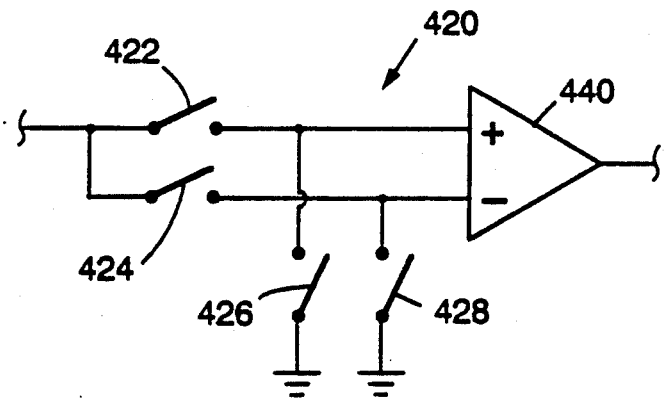
FIG. 9 is a schematic diagram of a synchronous demodulator used in the circuitry of FIG. 7.

A schematic diagram of the synchronous demodulator 420 is shown in FIG. 9. As shown in FIGS. 7 and 9, the output of the synchronous demodulator 420 is provided as input to a DC amplifier 440. The demodulator includes four switches 422, 424, 426 and 428, which are controlled in a conventional manner to open and close in response to the sign of the input to the demodulator. In the preferred embodiments, the switches 422, 424, 426 and 428 are CMOS devices, although they could alternatively be bipolar devices. When positive input—i.e. a positive portion or lobe of the AC wave input—is received by the demodulator 420, switch 422 is on (i.e. closed) to feed the positive signal into the positive side of the amplifier 440. Switch 424 is off (i.e. open) to prevent the signal from reaching the negative side of the amplifier 440. Switch 426 is off, again to allow the positive signal to reach the amplifier 440, and switch 428 is on, in order to prevent any other signal, such as unwanted spurious signals, from reaching the negative side of the amplifier 440.

Conversely, when a negative input in received by the demodulator 420, switch 422 is off, switches 424 and 426 are on, and switch 428 is off. This feeds the negative signal to the amplifier 440, while preventing any signal from reaching the positive side of the amplifier. The result of this configuration is that the demodulator 420 has the effect of rectifying the input thereto. Rectification can, of course, also be accomplished with a diode, but the output will not be synchronous, that is, it will not maintain the phase characteristics as accomplished by the demodulator 420.

The demodulator 420 thus eliminates components of the input signal which are out of phase, and external noise not synchronous with the oscillator output is eliminated. The result is that the output of the synchronous demodulator 420 is the DC equivalent of the sine wave output from the capacitance bridge 340, wherein the amplitude is proportional to the amplitude of the AC signal, and therefore proportional to the change in capacitance of the variable capacitor 220.

The amplification by the amplifier 440 is preferably relatively small in order to prevent amplification of parasitic DC parameters, such as DC bias inherent in the devices used. The gain of the amplifier 400 may on the other hand be relatively large (and in the preferred embodiment gain of about 30 is used), since DC offset bias is effectively rejected in an AC carrier system.

The output of the amplifier 440 is then preferably passed through a low pass filter 450, in order to in effect average out the wave, giving a true DC equivalent thereof, and further excluding unwanted noise from the signal.

The signal is then input to a voltage-to-frequency converter 460 which is a simple, low cost way to feed the signal into the microprocessor 470. Alternatively, an analog-to-digital converter could be used for feeding digital data in a serial or parallel bit stream, with the digital numbers being proportional to the DC signal input. The microprocessor 240 is preferably a processor such as the INTEL 80C39. A single-line bit port is utilized for feeding in the output from the converter 460.

As mentioned above, the capacitance bridge 340 is given a slightly positive DC offset voltage when the vessel 90 is empty. This is done in order to accommodate any lack of tolerance of the voltage-to-frequency converter 460 to negative voltages. If the potential difference between points A and B in FIG. 8 is exactly zero when the vessel 90 is empty, it is possible that DC bias somewhere in the system could actually make the voltage output from the amplifier 440 become negative, when it should be zero. Thus, a slight offset bias of approximately 170 mV in the preferred embodiment is utilized. Because of the offset bias induced by the trim capacitor 390, the amplifier 440 has a small output even when the vessel 90 is empty.

The microprocessor 470 samples the output of the voltage-to-frequency converter 460 at regular intervals. The output of the converter 460 is essentially a square wave signal with a frequency proportional to the voltage which was input to the converter 460. The input to the converter 460 should, as noted above, being nonnegative, and therefore the output of the converter 460 is preferably a signal with amplitude between zero and 6 volts, where approximately 3 volts represents a "zero crossing" or frequency transition.

The microprocessor 470 includes an internal counter governed by an internal clock, with the counter generating bits related to the frequency readings at the input. The clock has a count rate which in the preferred embodiment is five counts per second, so that each count is taken one-fifth of a second after the preceding count. Typically, the frequency of the input may be 5 to 40 kHz, and thus at a counting rate of five times per second, counts of 1,000 to 8,000 may be expected. For this reason, the internal counter of the microprocessor 470 preferably has 16 bits available for each one-fifth second count, with a minimum of 13 bits being necessary to accommodate 8000 binary-encoded counts (since $2^{13} = 8192$).

The functions of the microprocessor 470 are controlled by a program stored in an EPROM (erasable programmable read-only memory) 480. As each one-fifth second reading is made by the microprocessor 470, the difference between the current count (which is related to the volume of fluid in the vessel, and therefore may be referred to as a volume reading) and the previous count is calculated. This differential count represents the change in volume between the times of the two intervals, and thus represents the flow rate for that period of time. The differential count may be referred to as a flow count or flow reading.

In order to effect the comparison of current and previous volume readings, an internal register (not separately shown) is provided in the microprocessor 470 for storing the previous volume reading at any given time, and the current volume reading for a given interval is substituted therefor as the next succeeding count is made.

The differential counts are stored in the RAM (random-access memory) 490. This is repeated for a predetermined length of time, preferably ninety seconds, since a patient will typically void in less than this time. Thus, a total of 450 counts, at five counts per second for ninety seconds, are taken of the frequency input to the microprocessor 470.

Included as Appendix A hereto is a copy of software code for the microprocessor 470 which may be utilized to implement the present invention.

A control panel 500 is provided for user interface with the present system, with interface circuits 510 for interfacing between the control panel 500 and the microprocessor 470. The control panel 500 preferably includes an ON switch, a RESET switch and a PRINT switch. In addition, lights are provided, including an ON light, a READY light, a COMPLETE light, and a LOW BATTERY light.

When the user of the system and the patient are ready to begin, the user presses the ON switch, at which time the microprocessor 470 goes through an initialization procedure, clearing the RAM 490, the various ports of the processor 470, and the output of the microprocessor 470. Other standard initialization procedures may be implemented. The internal counter of the microprocessor 470 is also initialized and, as noted above, is programmed for making counts every fifth of a second, by way of clock interrupts.

After initialization, the the power for the analog circuitry (i.e., the circuitry including the devices shown in FIG. 7 between the capacitor 220 and the converter 460, inclusive) for the system is turned on by the microprocessor 470. Preferably the system is driven by battery power for independence from AC outlets; and thus, postponing the turning on of the analog power saves battery life. The battery is then automatically checked, and if the voltage is low, the LOW BATTERY light is turned on, and the procedure is halted. The microprocessor 470 may be programmed to wait a certain period of time for the analog circuitry to stabilize (ten seconds usually being sufficient), and implement another battery check, again turning on the LOW BATTERY light if the voltage is low.

If the battery voltage is sufficient, the microprocessor 470 then checks for whether a vessel 90 is in place. If no vessel 90 is in place in the adaptor 70, then the capacitor 220 will be missing from the bridge circuit 340, and the circuit 340 will be seriously out of balance. This will result in a frequency input to the microprocessor 470 considerably out of the expected range, which may, for instance, be 2 to 9 kHz. If no vessel 90 is detected, the READY light is flashed or blinked on and off repeatedly to indicate this.

Meanwhile, the battery is checked again, since it is now under load, and again, if the voltage is low, the LOW BATTERY light flashes on and off, and the procedure is interrupted.

If the vessel 90 is in place, and the battery is found to be in good order, then the microprocessor 470 stores (in the RAM 490) the initial count rate as the count relating to the initial volume of zero in the vessel 90. (Even with the vessel empty, this initial count will be nonzero, because of the offset bias in the capacitance bridge 340.) This automatically accounts for any differences in tolerances of the variable capacitor 220, which may result in slightly different "zero" frequency counts to the microprocessor 470 for each disposable collection system 30. In effect, storing the initial count rate as the empty-vessel reading calibrates the system for the upcoming measurements of flow rates and total flow volume. Then the READY light is turned on (but not flashed, as when there was no vessel 90 in place).

The microprocessor 470 then initializes the RAM 490 to its initial address, and a loop is implemented by the program in the EPROM 490 to detect when the patient begins voiding. In order to do this, the microprocessor 470 determines when a change in the frequency count obtained from the converter 460 occurs. Preferably, a minimum difference in counts between successive fifth-second counts at the microprocessor 470 input is awaited, such as a minimum difference of 4 counts, which in the preferred embodiment relates to a flow of 2 milliliters per second. The relation between the number of counts and the actual volume of fluid in the vessel may, of course, be calibrated differently if desired.

Once again, while the minimum difference is awaited, the battery is checked as above.

Once the minimum difference is detected, the READY light is turned off, and an optional MEASURING light on the control panel 500 may be turned on. At this point, the microprocessor 470 begins storing the one-fifth second differential counts (i.e. the flow readings) into the RAM 490. The above-mentioned internal register is used by the microprocessor 470, so that when the minimum difference mentioned above is detected, the count previous to that which resulted in the minimum difference may be stored in the RAM 490, for later use in determining the total flow volume.

The program from the EPROM 480 then implements a loop for measuring and storing the incoming flow readings into the RAM 490. This loop is represented in the flow chart of FIG. 11. In this portion of the program, the current counts for a one-fifth second interval are obtained from the converter 460 by the microprocessor 470. As noted above, the microprocessor begins to store the flow data as soon as a minimum difference between two successive counts is detected.

The program will also compare successive volume readings to determine whether a given volume reading for a fifth-second interval is less than that of the interval before. Since the capacitance of the capacitor 220—and hence the DC voltage output from the amplifier 440 and the frequency output from the converter 460—is proportional to the total amount of fluid in the vessel 90, as the vessel fills up the frequency output from the converter 460 should rise continuously. However, there will necessarily be motion of the fluid 130 in the vessel 90, and therefore wave action or other disturbances may cause the amount of fluid 130 in the vicinity of the capacitor 220 to be less at a later time (when the vessel 90 actually has more fluid in it) than at an earlier time. Such wave action would therefore introduce errors into the data; and since it is certain that the amount of fluid 130 in the vessel 90 at a later time is always at least equal to the amount of fluid present at an earlier time, the program is designed to correct for this type of error. Therefore, if the volume reading for a given interval is less than the volume reading for the preceding interval, then the current differential reading is set to equal to the previous differential reading. The effect of this is to create a presumption that the flow remained constant for that interval (since it could not have been negative, and was presumably not zero). Although this may not precisely reflect the actual flow of fluid into the vessel 90, as a result of the error introduced by wave action, as will be seen in the discussion below regarding post-processing of the data, any error introduced into the flow data is minimized by the post-processing of the data. Also, the total volume reading which is finally obtained is not affected at all, since the calculation for the total volume reading is based solely upon the initial and final volume counts.

The differential counts are then converted to the chosen calibration of a display device such as printer 520. For instance, if the printer is a dot matrix printer, the data may be calibrated to store a certain number of dots per frequency count obtained from the converter 460.

Preferably, the program includes a routine to correct for various shapes of vessels 90. For instance, since the sides of the vessel 90 as seen in FIGS. 2 and 3 are sloped outwardly (relative to the bottom of the vessel), a frequency count increase (which relates to an increase in volume of the fluid 130 in the vessel 90) will be less at a later time than at an earlier time for a given increase in volume of the fluid, since the height of the fluid will rise less where the walls are farther apart, namely at the upper end of the vessel 90. Therefore, the program corrects for this in the following manner. As noted above, the frequency from the converter 460 is proportional to the total amount of fluid 130 in the vessel 90. Thus, where the frequency is low, a difference between two successive interval counts will indicate a lower total volume change than the same count difference when the total volume is greater. Therefore, the program is designed to determine the total frequency count, and for a given frequency count, to then determine by means of correction factors what total volume change the count difference between two successive intervals represents. This is done the entire time the data is being processed during the ninety-second test.

The correction factors for the vessel 90 may be determined in either empirically or mathematically. For instance, for the generally conically-shaped vessel such as vessel 90, it is straightforward and well-known to calculate the changes in volume as the vessel fills with a fluid as a function of the height of the fluid within the vessel. For more complicatedly shaped vessels, an empirical determination of this function may be preferable. The correction factors are stored as part of the program, either in the form of conversion tables or as a conversion formula.

Once the flow counts have been calibrated and corrected, they are stored in the RAM 490, and the process is repeated for the ninety-second test period or until the test is interrupted by the user (such as by pressing the PRINT switch). The loop is then exited, the MEASURING light is turned off and the COMPLETE light is turned on. At this point, the volume count for the last one-fifth second interval for which a measurement was taken is stored as representing the final volume of the fluid 130 in the vessel 90. The internal timer for the microprocessor 470 and the counter are then automatically switched off, as is the power to the analog circuitry.

At this point, in the RAM 490 are stored the flow counts for the entire test, corrected and calibrated as noted above, as well as the initial and final volume counts, each of the stored counts is correlated with the interval to which it pertains. A post-processing loop is then implemented, as represented in the flow chart of FIG. 12. The need for the post-processing loop is explained by reference to the graph shown in FIG. 13, which is based upon actual data. As mentioned above, the flow rate of fluid 130 into the vessel 90 is represented by the successive differences between counts obtained from the converter 460. Curve 530 shows the flow output from a test pump which is designed to produce a constant flow. Thus, flow begins at time zero, increases to a certain constant, and then diminishes after a given period of time. However, when fluid (whether from a pump or from a patient) reaches the vessel 90, it changes the effective geometric configuration of the variable capacitor 220, because of the fluid's conductive properties. Thus, the capacitance value of the variable capacitor 220 changes very quickly at first, causing a spike in the data. A representative graph of the actual, unprocessed data from a constant flow pump appears as curve 540 in FIG. 13, with the peak of the spike being designated as 550.

The spike 550 in the unprocessed flow data is typically followed by a trough 560, which is a result of the artificially high spike 550; since the spike 550 caused inaccurately high frequency counts, the actual frequency counts later obtained will seem to indicate a large drop in the flow rate, when in fact, in the example given, the flow rate is constant. The "hook" in the curve 540 caused by the spike 550 and trough 560 is a problem resulting from the use of variable capacitors such as capacitor 220 in conjunction with a dielectric such as a fluid which actually may conduct current. This type of erroneous output has heretofore made the data obtained at the beginning of the flow period unusable, and because of this, the use of a variable capacitor in a fluid monitoring system has heretofore been impractical and unreliable. The problem is now solved by the present method of post-processing the flow data, as described in detail below.

The actual flow output of a patient during voiding will not be constant, as represented by curve 530, but more typically resembles a bell curve. However, the same type of "hook" error is introduced no matter what the actual flow of the pattern is; and the data errors discussed above are resolved by the present method for any flow pattern.

The post-processing method corrects for errors in the flow readings in three basic steps. First, retrospective averages for the flow readings of a first predetermined block of the intervals are generated, and prospective averages for the flow readings for a second predetermined block of the intervals are also generated, where the second block has an overlap with the first block. Then, combined averages are generated for the intervals relating to the overlap, the combined averages being derived from the retrospective averages and the prospective averages. The post-processing results in the generation of error-corrected averages, with one such error-corrected average relating to each of the predetermined intervals, which are then substituted for the flow readings in the memory.

The post-processing is carried out as follows, and is best understood by reference to the curves shown in FIG. 14, which are based upon actual data. Each of the retrospective flow averages is generated by first generating a retrospective total of the flow readings from the first interval through the Ith predetermined interval—where I is a variable integer between 2 and a first predetermined constant J—and then dividing the retrospective total by I, and repeating the step of generating such retrospective averages for each I between 2 and J. In the preferred embodiment, J equals 24, and thus 23 retrospective averages are generated, one for each of intervals 2 through 24. (The first interval flow reading is unaltered.)

Figure 13:
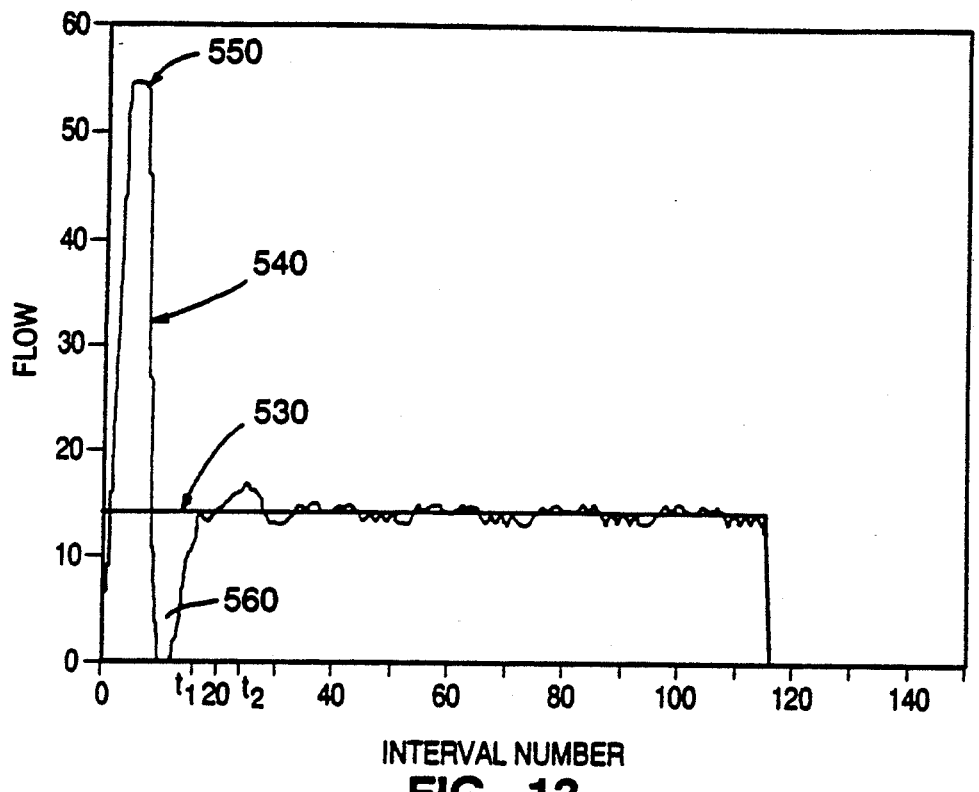
FIG. 13 is a graph showing the flow output of a constant-flow pump and the unprocessed data for such a pump.

The time up through which the retrospective averages are taken is represented in FIG. 13 by $t_2$, and for this example represents 4.8 seconds worth of data (i.e., twenty-four count intervals). Thus, in order to take the retrospective averages between time zero and the 24th interval, the stored flow counts are totalled, and this total is divided by the interval number for the current count. For the seventh interval, the first seven counts are added, and this total is divided by seven. At the sixteenth interval, an average of the first sixteen data counts will be calculated, and so on through the 24th interval.

The prospective averages for the intervals between (J-K) and (N-K) are then generated, where N is the total number of intervals (450 in the preferred embodiment) and K is a second predetermined constant, equalling 7 in the preferred embodiment. Each of the prospective averages is generated by first generating a prospective total of the flow readings from the Lth interval through the (L+K)th interval, where L is a variable integer between (J-K) and (N-K). Thus, in this example, (J-K) is 17, (N-K) is 443, and L goes from 17 to 443. The first prospective average is therefore the average of the flow readings for the eight intervals intervals 17 (represented in FIG. 13 as $t_1$) through 24 (or $t_2$), and prospective averages are generated for each of the succeeding intervals through the end of the data, in each case taking the average of a given interval and the seven succeeding intervals. Of course, for the 444th through the 450th intervals, their are fewer than seven succeeding intervals, and the flow readings from these intervals are utilized only to the extent that they affect the prospective averages of intervals 436 through 443. In practice, a patient virtually never requires the full 90 seconds to void, so that there are in any case no flow readings relating to these intervals.

As the retrospective averages for intervals 1 through 16 (which equals J−(K+1)) are generated, they are stored in the RAM 490 in place of the flow readings appearing therein for those intervals. As the prospective averages for intervals 25 through 443 (i.e., J+1 through N-K) are generated, they are likewise stored in memory in place of the flow readings for those intervals. For the intervals 17 through 24 (i.e., J-K through J), the retrospective and prospective averages are first merged, according to the method represented in FIG. 12, and the combined averages are then substituted for the flow readings in memory relating to those intervals.

Figure 12:
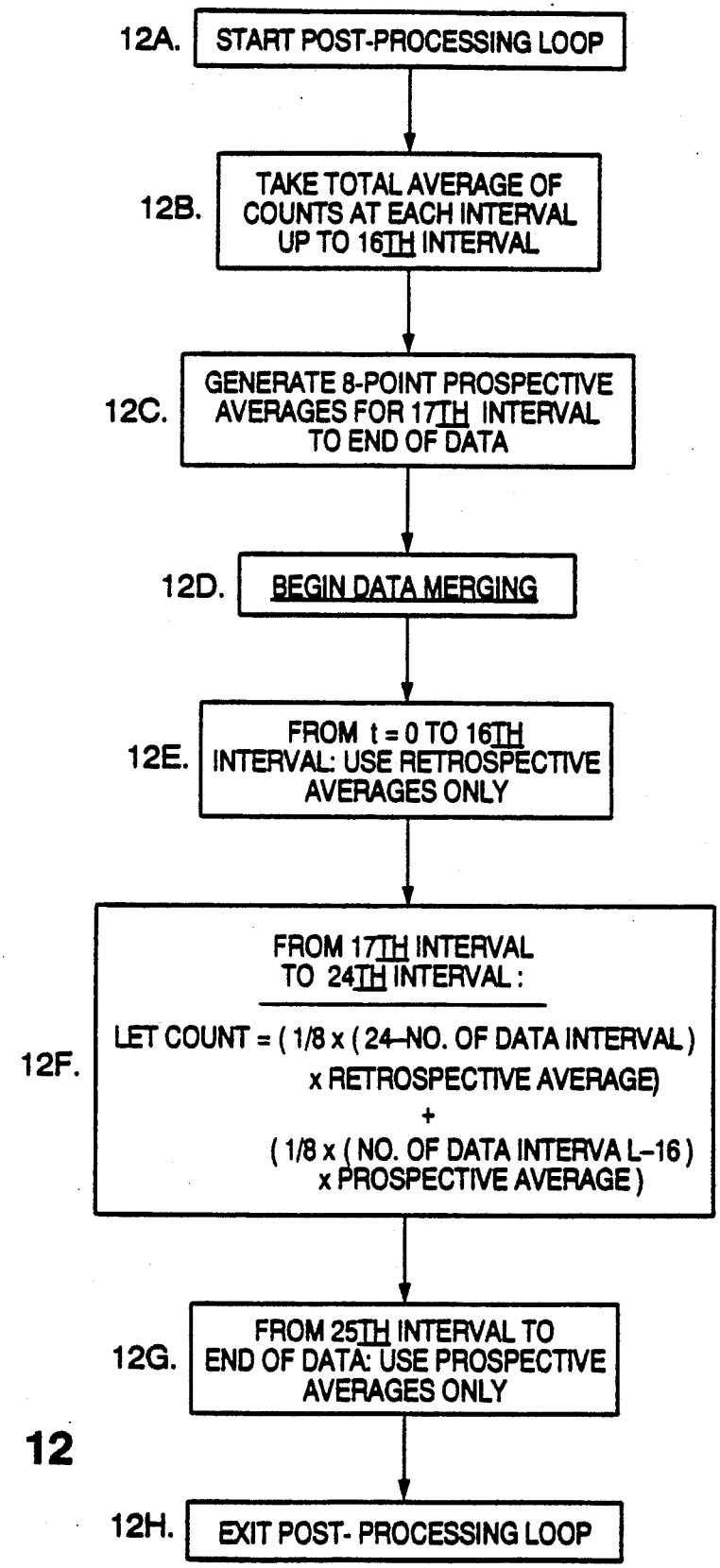
FIG. 12 is a flowchart of a post-processing loop utilized by the invention.

The method of the merging of data between the 17th and 24th data intervals as shown in FIG. 12 is as follows. Each of the combined averages is generated by adding a fraction (J−M)/(K+1) of the retrospective average to a fraction (M−(J−(K+1)))/(K+1)) of the prospective average, where J and K are the predetermined constants mentioned above (24 and 7, respectively), and M is the number of the interval (which may be expressed as going from (J-K) to J, i.e. 17 to 24). Thus: (J-M) goes from 7 to 0 as M goes from 17 to 24; M−(J−(K+1)) goes from 1 to 8 as M goes from 17 to 24 (and as (J-M) goes from 1 to 7); and the denominator (K+1) equals 8. This may be expressed as:

$$CA = ((J-M)/(K+1))RA + (M-(J-(K+1)))/(K+1))PA$$

where CA is the combined average, RA is the retrospective average, and PA is the prospective average. With the values discussed herein, the following combined averages are generated:

| Interval Number | Combined Average |
|---|---|
| 17 | 7/8(RA) + 1/8(PA) |
| 18 | 6/8(RA) + 2/8(PA) |
| 19 | 5/8(RA) + 3/8(PA) |
| 20 | 4/8(RA) + 4/8(PA) |
| 21 | 3/8(RA) + 5/8(PA) |
| 22 | 2/8(RA) + 6/8(PA) |
| 23 | 1/8(RA) + 7/8(PA) |
| 24 | 0/8(RA) + 8/8(PA) |

As the combined averages are generated, they are substituted for the flow readings in the RAM 490.

Of course, any of the variables and constants discussed above may be altered as desired, but it has been determined experimentally that the above values generate quite accurate results. Also, other details of merging the retrospective and prospective averages may be implemented without affecting the qualitative result.

Figure 14:
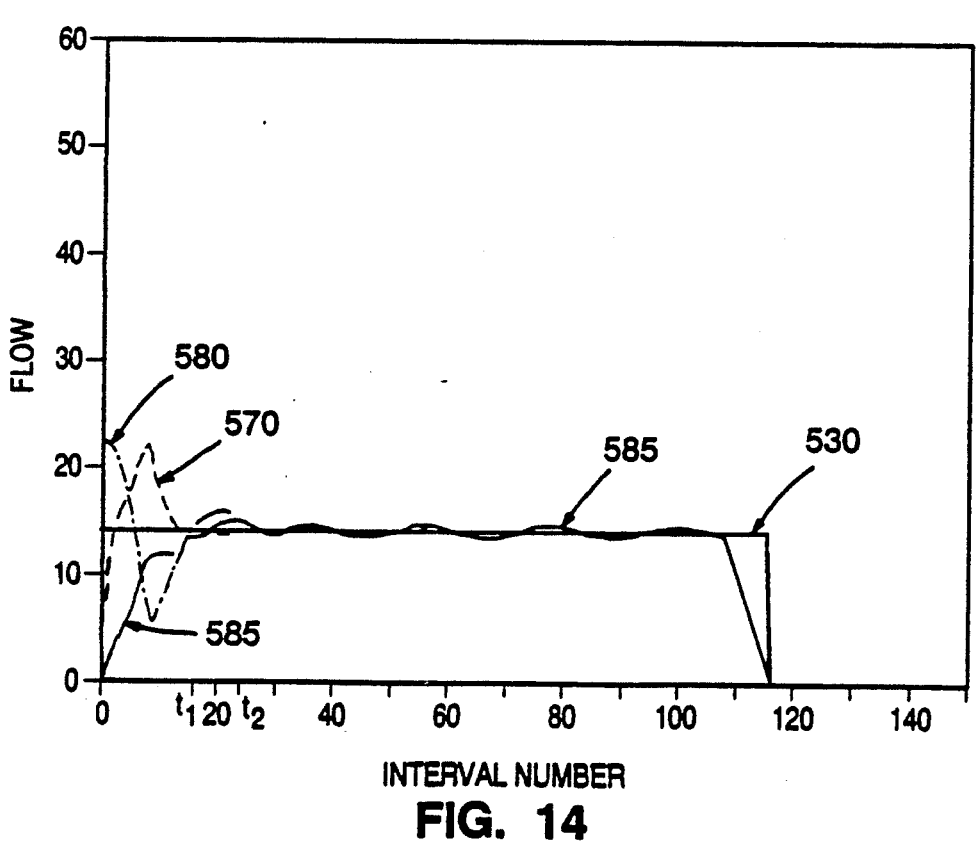
FIG. 14 is a graph showing the steps in post-processing for the data of FIG. 13.

The results of the data merging steps for the curve 530 are shown in FIG. 14. A graph of the retrospective averages from time zero to $t_2$ is approximately shown as curve 570, while a graph of the eight-point prospective averages is approximately shown as curve 580. It will be noted that the retrospective averages curve of 570 lags the actual curve 540 from the data received, while the prospective averages curve 580 leads the curve 540, since the prospective averages in effect anticipate upcoming data. The retrospective, prospective and combined averages generated by the merging of the retrospective and prospective averages are shown as error-corrected curve 585 of FIG. 14, which demonstrates that the method described above results in the elimination of the spike 550 and trough 560, and produces a result much more closely matching the actual output curve 530. (Incidentally, although the prospective average curve 580 is shown from time zero for illustration purposes, this prospective average is not actually utilized in the data merging until time $t_1$.)

Thus, in practice it has been found that utilization of the post-processing of the data by the method shown in FIG. 12 results in experimental curves very closely matching known flow patterns, such as the flow data represented by curve 530 for a constant-flow pump. This post-processing of data has also been performed on data relating to a bell-shaped curve such as a curve actually resulting from micturition, with results similar in accuracy to the constant-flow curve. Indeed, in the case of a bell-type curve resulting from actual urine flow data the match is even closer, for the following reason: as discussed above, the spike 550 and trough 560 are a result of the sudden effective alteration in the geometric configuration of the electrode 220 upon being contacted by fluid. If the actual flow at the beginning of data gathering is relatively low, the spike will be concomitantly low; and the converse is true. Therefore, since a constant-flow pump by definition has an initial output which is significantly large relative to its average output (indeed, it is equal thereto), the spike 550 is also large. However, human urination is such that the initial flow is small, and a maximum is reached, and the flow tapers off again—hence, the bell-shaped curve. Thus, the effect of the spike 550 and the trough 560 on the error-corrected curve 585, being at the beginning of the data, is less significant than for the constant-flow data represented in FIG. 14.

Once the post-processing loop is completed, the microprocessor 470 makes certain calculations for outputting data of importance to the physician. For instance, the peak flow rate is calculated, by storing the highest flow reading detected. Preferably, an average of the five flow readings around this highest flow reading (including the highest flow rate itself) is taken as the peak flow rate.

The time to peak flow is also calculated. The number of count intervals to peak flow is simply divided by five to determine number of seconds to peak flow (since there are five counted intervals per second).

The total voiding time is also preferably calculated, by dividing the time during which micturition was taking place by five, to obtain voiding time in seconds. It should be noted that there may be intervals between time zero and the end of the test during which no micturition is taking place. The program accounts for this in determining the voiding time by ignoring intervals during which no change in the total volume of the fluid 130 (and hence change in the capacitance value of the variable capacitor 220) was taking place. This accommodates stops and starts during micturition by the patient.

The total volume of urine 130 received by the vessel 90 is also calculated, by subtracting the initial (calibration) volume count—which relates to zero volume of fluid 130 in the vessel 90—from the final volume count.

Finally, the average flow during voiding is calculated by dividing the total volume by the total voiding time as described above. The total volume calculation will, of course, depend upon the vessel correction factor discussed above, the step for which appears in FIG. 11.

Each of the parameters calculated as described above is then converted to a number relating to the desired dimensions for printout purposes. For instance, the total volume may expressed in milliliters, and for this purpose an appropriate conversion factor converting the counts to a numeral relating to actual milliliters of fluid 130 in the vessel 90 is utilized. Similarly, the average flow may be in milliliters per second, and so on. Alternatively, each of the conversions of the data may be carried out before storing the data in the RAM 490; for instance, the error-corrected flow averages generated by the post-processing method may be calibrated for the printer either before or after storage in memory. An advantage of doing so beforehand is that the time it takes to print out the data is substantially decreased, since no extra time is needed by the microprocessor 470 for conversions.

Finally, when the user presses the PRINT switch, the flow versus time graph is printed by the printer 520, and the parameters calculated above are printed out as well. A sample of the urine 130 is then obtained as described above by the evacuating device 200, the drain 160 is opened to dispose of the unwanted portion, and the physician or assistant disposes of the used urine collection system 30.

Figure 15:
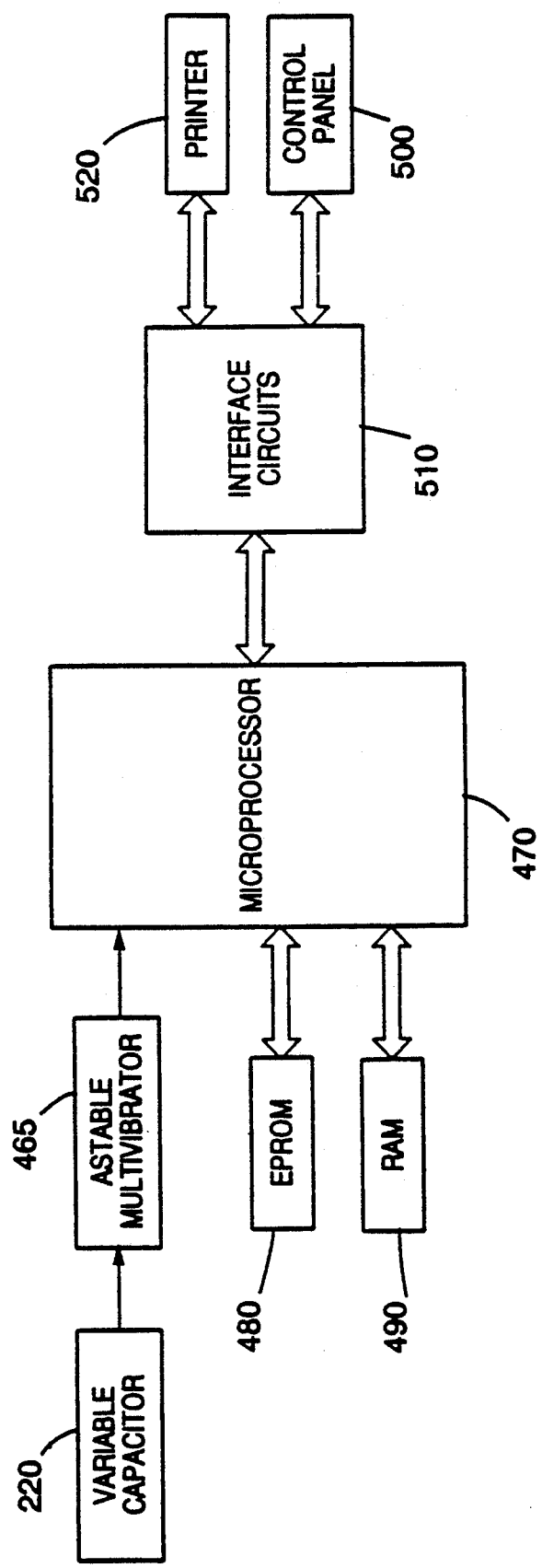
FIG. 15 shows an alternative embodiment of the block diagram in FIG. 7.

Another embodiment of the electronics of FIG. 7 is shown in FIG. 15. In this version, blocks 340 through 460 are replaced by a single circuit. This circuit is an astable multivibrator 465 that uses variable capacitor 220 to determine its operating frequency. The astable multivibrator includes a single integrated circuit comparator (not separately shown) and a second comparator used as a buffer to isolate the first one from line loading effects. Unlike the voltage-to-frequency converter, it produces a frequency that is inversely proportional to the fluid level in the vessel 90. That is, instead of producing a frequency of, for example, 5 kHz increasing to 40 Khz as the vessel fills, this circuit produces a frequency in one embodiment of 40 kHz, decreasing to 10 kHz as the vessel 90 fills with fluid.

Figure 11:
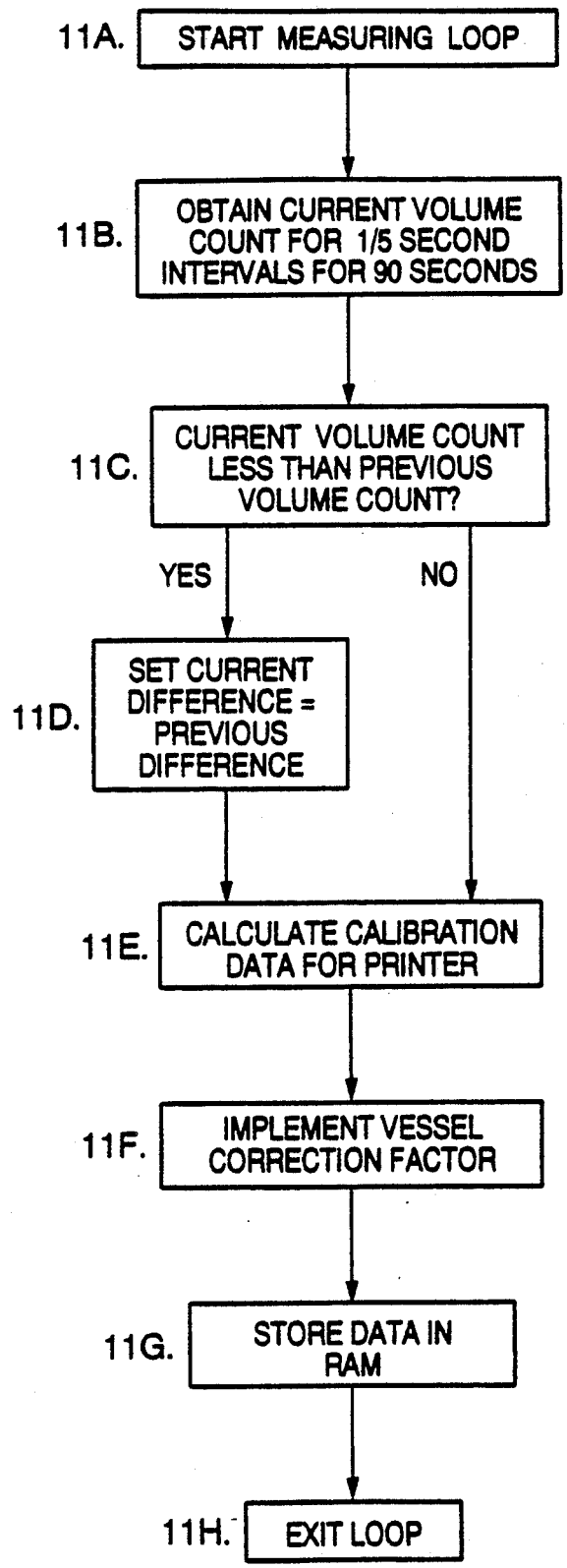
FIG. 11 is a flowchart of a measuring loop utilized by the invention.

This requires a slight change in the software measuring loop shown in FIG. 11 to accommodate for the differences noted above, in that different steps will be taken to obtain the current volume count for each interval. Other than this change, all of the processing may be the same.

In an alternative embodiment of the circuitry represented by FIG. 15, a sensor interface circuit 467 (shown in FIG. 16) may be connected between the astable multivibrator 465 and the microprocessor 470. This circuit uses digital counters to produce an increasing frequency as the vessel fills with fluid, even though the sensor electronics produce a decreasing frequency. In this embodiment, the software measuring loop may be the same as that shown in FIG. 11.

Figure 17:
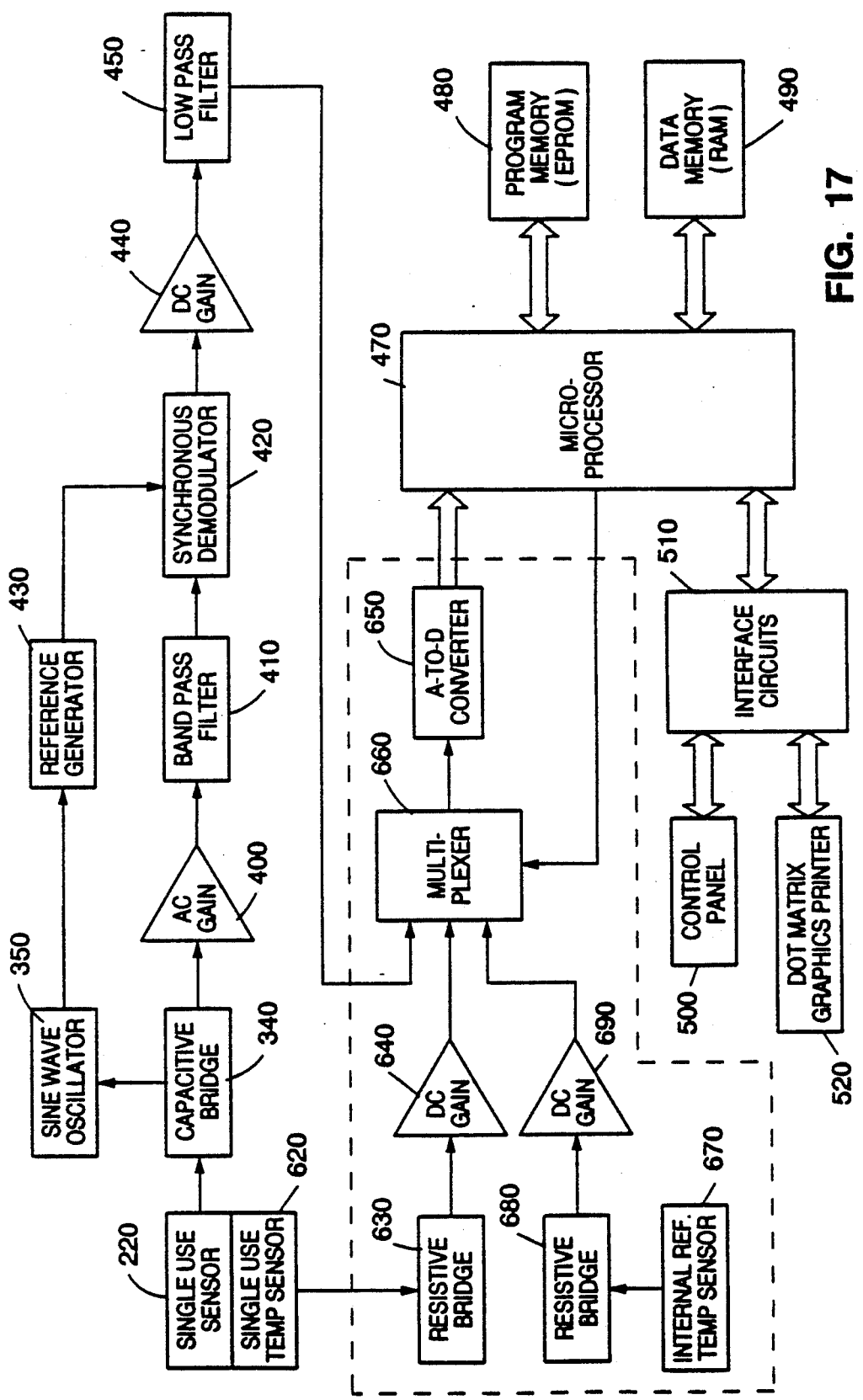
FIG. 17 is a block diagram of an alternative embodiment of the invention utilizing temperature sensing.
Figure 18:
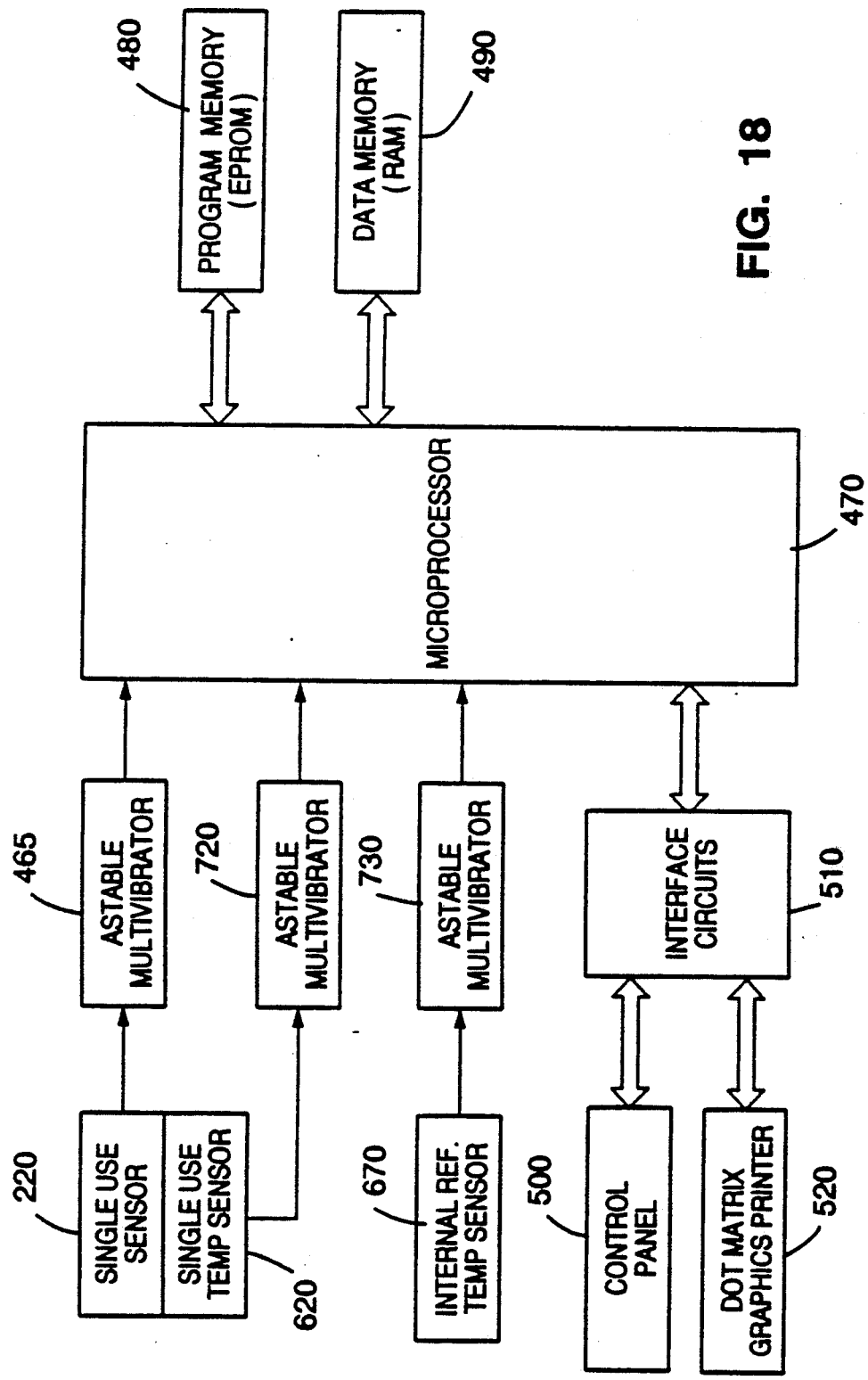
FIG. 18 is an alternative embodiment of the block diagram of FIG. 17.
Figure 19:
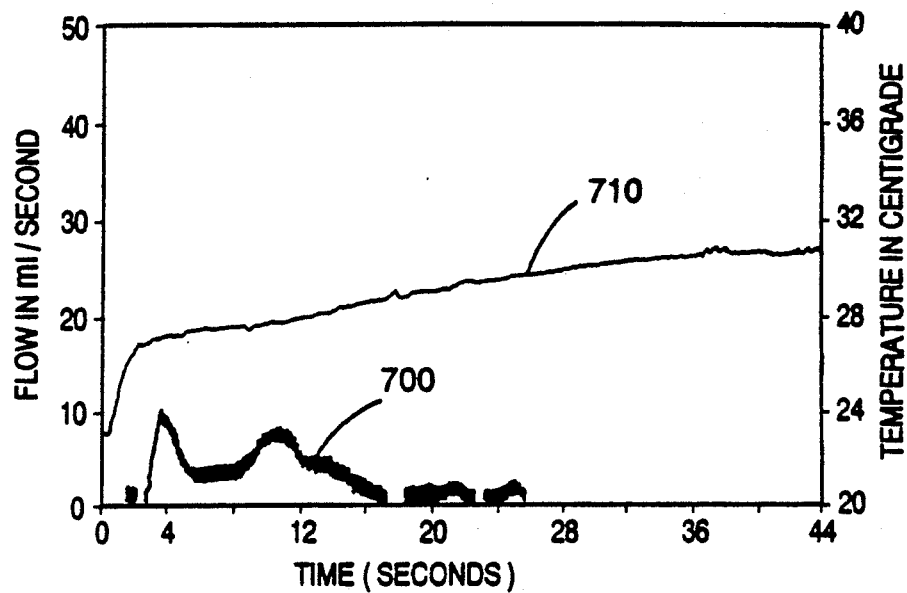
FIG. 19 is a graph of actual test data showing temperature and flow rates as a function of time utilizing the system of the invention.

FIGS. 17-19 of the drawings relate to an alternative embodiment of the of the invention, wherein the above-described embodiments are adapted to include temperature-sensing capability. This embodiment provides simultaneous measurement of flow rate and temperature of the sample as a function of time. Referring to FIG. 3, a thermistor 610 is attached to the vessel 90 at a point near its bottom. Alternatively, the thermistor 610 may be attached to a side of the variable capacitor 220. In the alternative embodiment of FIG. 5, the thermistor 610 may be attached as shown at the interior of the vessel 90. It is preferable that the thermistor 610 be situated at or near the bottom of the interior of the vessel 90, as shown in FIGS. 3 and 5, so that it will begin to sense the temperature of the fluid immediately upon beginning of urination. In FIG. 3, two alternative placements for the thermistor 610 are shown.

Referring to the block diagram of FIG. 17, this represents a modification of the circuitry represented in the block diagram of FIG. 7, so as to include temperature sensing capability. Thus, a temperature sensor 620 is utilized, and is shown adjacent the variable capacitor or single use sensor 220. The temperature sensor 620 is coupled to a resistive bridge 630 which has an output coupled to an amplifier 640.

The resistive bridge 630 produces an electrical signal from the temperature sensor 620 which relates directly to the temperature sensed thereby. The output of the bridge 630 is fed into the amplifier 640, whose gain is set to provide a signal of an appropriate amplitude. The output signal from the amplifier 640 is fed into an analog-to-digital converter 650 via an analog switch or multiplexer 660. The converter 650 is utilized to convert the signal into a form suitable for the microprocessor 470.

The room temperature is measured utilizing an internal temperature measuring device such as internal reference temperature sensor 670, which is coupled to another resistive bridge circuit 680, which has an output coupled to an amplifier 690, whose output is coupled to the multiplexer 660. The reference temperature sensor 670 thus provides a signal to the microprocessor 470 which may be used as a reference for calibrating the signal from the temperature sensor 620. In practice, if the temperature detected by the sensors 670 and 620 does not change for a certain period of time, such as thirty seconds, then the temperature value detected by the sensor 670 is taken as room temperature, and the microprocessor accordingly calibrates any temperature values sensed by the sensor 620. This way, a more accurate sensor may be used for the sensor 670, and a less expensive sensor may be used for the sensor 620, which is advantageous because the sensor 620 may be disposed of after a single use. The internal reference temperature sensor 670 is preferably located on the outside of the commode adaptor.

Figure 22:
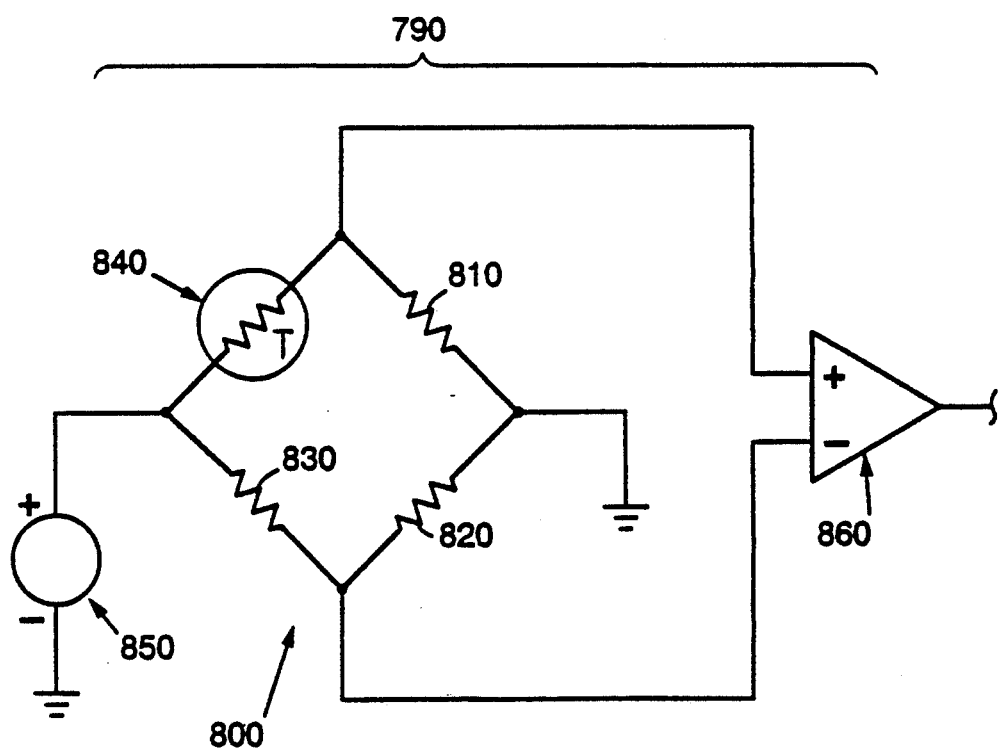
FIG. 22 is a schematic diagram of a resistive bridge circuit for temperature sensing in the invention.

The bridge circuit 790 shown in FIG. 22 may be used for the circuit shown in FIG. 17. In FIG. 22, a resistive bridge circuit 800 is utilized, having fixed resistors 810, 820 and 830, and a thermistor or temperature-dependent variable resistor 840. A power supply 850 (which may be A.C. or D.C.) is provided for powering the bridge 800, and the output of the bridge is provided as input for an amplifier. Thus, the circuit 790 may be used in place of elements 670, 680 and 690 of FIG. 17, and also in place of elements 620, 630 and 640.

Other than the differences noted above, FIG. 17 may be essentially identical to the block diagram shown in FIG. 7. When urination begins, the temperature sensed by the sensor 620 is input to the microprocessor 470 as a digital signal from the converter 650, and is stored in the memory as a function of time, simultaneous with the storing of the flow rates as calculated by the microprocessor 470. An actual result of such simultaneous data gathering is shown in FIG. 19, where the flow rate curve 700 and temperature curve 710 are plotted together. As seen from curve 710, the temperature begins at a minimum amount, which is less than body temperature, because initially the heat of the fluid is absorbed by the vessel 90 which will typically be at room temperature. As increased amounts of fluid enter the vessel 90, the temperature slowly climbs.

It will be appreciated that it would be quite difficult to imitate both the flow rate data and the temperature data artificially, and thus the apparatus described provides a reliable means for screening out nongenuine urine samples. The system of the invention thus measures the temperature of the fluid immediately upon the beginning of voiding, and at regular intervals from approximately one minute to several minutes thereafter. The shape of the curve shown in FIG. 19 will depend upon the initial temperature and the nature of the fluid and the test equipment, and on the temperature of the room. Comparing a test profile against known normal data (such as FIG. 19) provides a validity test of the patient's micturition.

Figure 16:
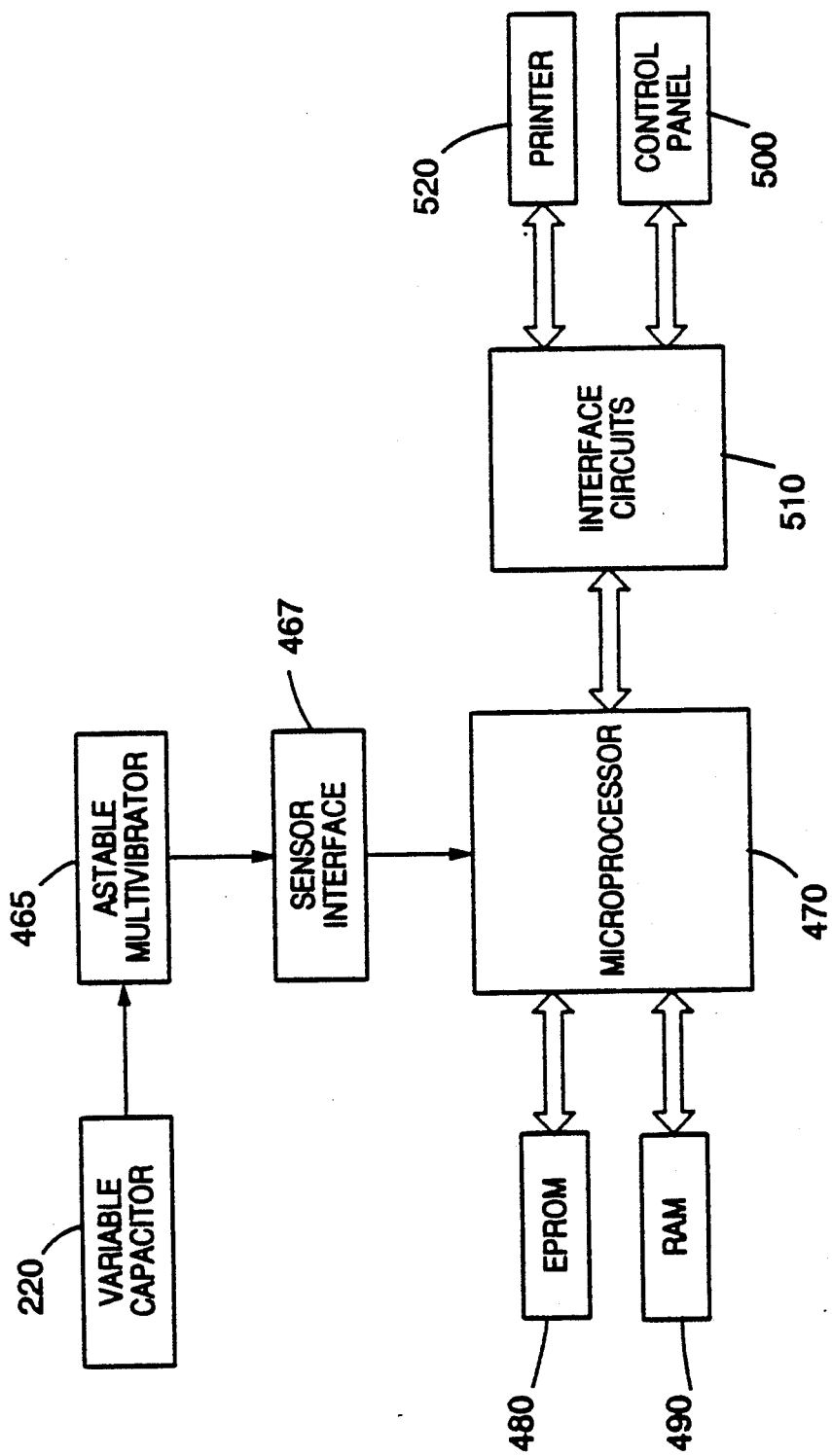
FIG. 16 shows an alternative embodiment of the block diagram shown in FIG. 15.

The block diagram of FIG. 18 shows an alternative to the diagram of FIG. 17, wherein, as with FIG. 16 vis-a-vis FIG. 7, the elements 340, 350 and 400–450 of the block diagram have been replaced by an astable multivibrator 465, and wherein the elements 630–640 have been replaced by an astable multivibrator 720. In addition, the elements 680–690 have been replaced by an astable multivibrator 730, and the multiplexer 660 and the A-D converter shown in FIG. 17 are not used in FIG. 18. As with the embodiment of FIG. 15, the astable multivibrators 465, 720 and 730 include single integrated circuit comparators (not separately shown). The block diagram of FIG. 18 may be modified to include a sensor interface such as sensor interface 467 shown in FIG. 16, for effectively inverting the signal from the multivibrator 465 to produce digital counts of increasing frequency as the vessel 90 fills with fluid.

In an alternative embodiment, a temperature probe may be utilized with the urine collection system 30, in place of the thermistor 610. If a thermistor 610 is utilized, and is attached as shown in FIGS. 3 and 5 to the vessel 90, it will be disposed of when the disposable portion of the collection system has been used. Instead of this, an infrared thermometer 740 is mounted to the outside of the commode adaptor 70, as shown in FIG. 2. The thermometer 740 includes a thermopile and an optics system (not separately shown). The thermopile is a collection of thermocouples fabricated utilizing integrated circuit technology, and the optical system includes one lens or a plurality of lenses which collect infrared energy from a region 750 near the bottom of the vessel 90. The thermopile included in the thermometer 740 produces a small voltage which is coupled into an amplifier, and is input as a digital signal (via an A-D converter such as converter 450) to the microprocessor 470, just as with the temperature sensor 620 shown in FIG. 17. Alternatively, the signal from the infrared thermometer 740 may be coupled by means of a voltage-to-frequency converter to the microprocessor 470.

In order for the region 750 to closely track the temperature of the fluid inside the vessel 90, region 750 is preferably relatively thin compared to the average thickness of the vessel 90, so that there is no appreciable time lag between temperature increase in the interior of the vessel 90 and temperature increase of the region 750. This thinning of region 750 is shown in dotted fashion in FIG. 3. The region 750 is preferably black in color, in order to radiate as much energy as possible. One way to produce such a section is to provide a hole in the area of region 750, and place a piece of black tape over the hole so as to seal it off from the passage of any fluid.

Alternative locations for the infrared thermometer are also shown in FIG. 2. For instance, an infrared thermometer 760 may be attached to the side of the vessel 90, and coupled into the circuitry of the invention as described above. In this embodiment, the thermometer 760 would be disposed of along with the vessel 90.

The infrared thermometer 760 may either be attached to the side of the vessel 90, or be suspended by a wire 770 or other suspension means from the commode adapter 70. In the latter embodiment, the thermometer 760 is reuseable, since it is not disposed of with the vessel 90, and may be placed directly adjacent a region of the vessel 90 for detecting temperature of the fluid therein, such a region being identical to the region 750.

Other alternative locations for the infrared thermometer are within the vessel 90 itself, within the commode adapter 220, or carried by the toilet underneath the vessel 90. These are not separately shown in the drawings.

Figure 20:
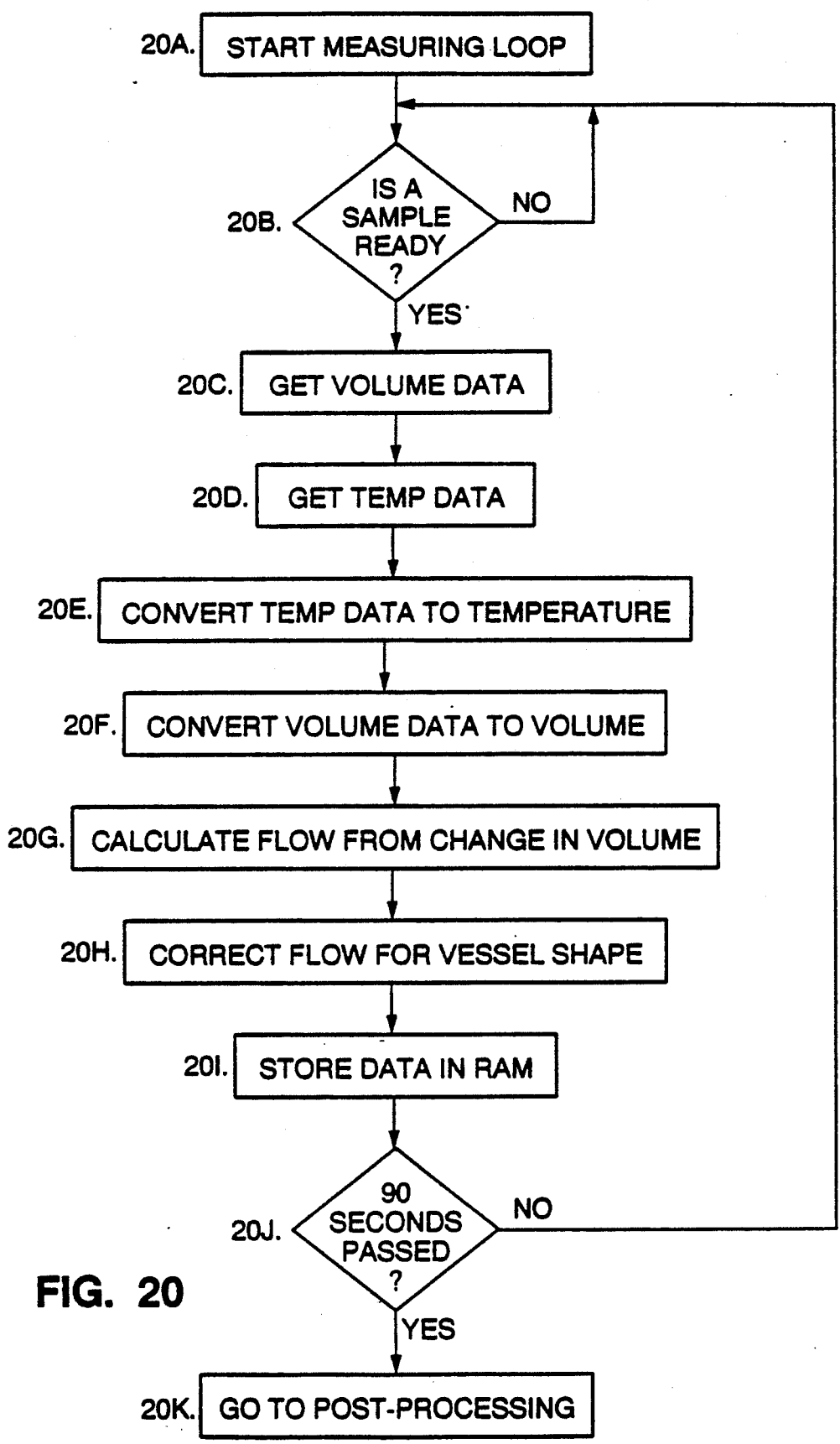
FIG. 20 is a flowchart of an alternative to the method shown in FIG. 11.
Figure 21:
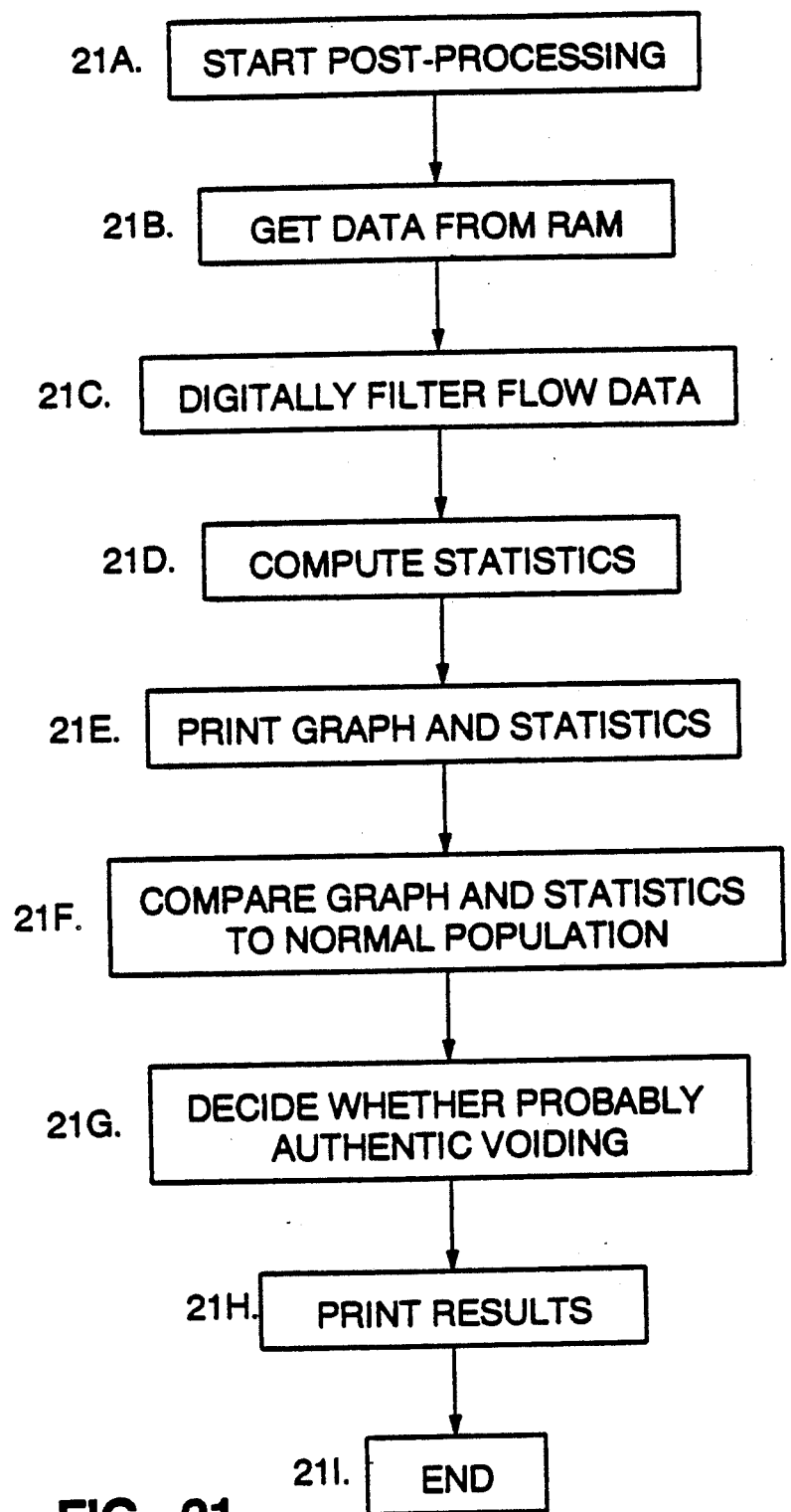
FIG. 21 is a flowchart of an alternative to the method shown in FIG. 12.

The temperature sensing embodiments of the invention utilize method steps which are somewhat different from those of the embodiments discussed above. These are represented in FIGS. 20 and 21. Thus, referring to FIG. 20, box 20A corresponds to box 11A of FIG. 11, and the following are also corresponding steps in the method of the invention, as represented in FIGS. 11 and 20, respectively: 11B/20C; 11C–11D/20G; 11F/20H; and 11G/20I; and 11H/20K. There is no calibration step (see box 11E) explicitly represented in FIG. 20, but this step will normally also be included as part of the method represented in that Figure, preferably just before box 20H.

Box 20B relates to a step for determining whether a sample is ready to be detected for carrying out the method of the invention. In the preferred embodiment, this comprises a timer set at 200 milliseconds, such that the subsequent steps of the method take place one-fifth of a second after the measuring loop is begun, and every one-fifth second thereafter.

The step represented in box 20D relates to obtaining temperature data from the circuit of FIG. 18 or from that of FIGS. 17 and 22. If the circuit of FIG. 18 is used, the data obtained in boxes 20C and 20D are in the form of frequencies, while if the circuitry of FIGS. 17 and 22 is used, the data is in the form of voltages.

Boxes 20E and 20F relate, respectively, to the conversion of the temperature and volume data to values for storage in the RAM, as indicated in box 20I. However, the volume data are first utilized to calculate flow values, and corrections are made for the particular vessel being used, as indicated by boxes 20G and 20H. Thus, the data stored in the RAM reflect both the temperature of the urine, as a function of time, and the flow rates of the urine during micturition.

FIG. 21 shows a flowchart corresponding to the flowchart of FIG. 12, but adapted for use in the embodiments of the invention which incorporate temperature sensing. Steps 12B through 12G may be included in the step represented by box 21D in FIG. 21, and the other steps of that Figure are self-explanatory. Thus, in step 21B, the data stored in the RAM in step 20I of FIG. 20I of FIG. 20 are obtained, and in step 21C, the data are filtered, which is carried out by the microprocessor.

In step 21D, the urine flow statistics described above relative to the earlier embodiments are calculated, such as peak flow, average flow, and time to peak flow. These are used for comparisons to patient norms, for authentication of the urine sample.

In step 21E, the microprocessor causes the printing of a graph (or other display) of the flow and temperature data, as represented in FIG. 19. These data are then preferably compared with standard or normal data, in step 21F, and in step 21G the processor determines whether the data are within acceptable limits, and are thus authentic. The comparison may be done by a least squares residual fit, or by some other standard method for comparing data for similarity. In step 21H, the result of the authentication process is displayed or printed out, and the method is completed.

What is claimed is:

1. An apparatus for measuring temperatures and flow rates of a fluid, comprising:
    a vessel including a wall defining an interior and an exterior, said interior for collecting an amount of the fluid;
    a first electrode comprising a first electrical conductor disposed adjacent said wall at said exterior;
    a second electrode carried in said interior of said vessel;
    a first dielectric disposed adjacent said first electrode for insulating said first electrode from said second electrode and from said fluid;
    a second dielectric disposed adjacent said second electrode and in communication with said vessel interior, such that said first and second electrodes and said first and second dielectrics together comprise a variable capacitor with a capacitance value which varies with said amount of fluid;
    means connected to said variable capacitor for determining the flow rates of the fluid as a function of said capacitance value and for providing an output reflecting said flow rates;
    means for displaying said flow rates;
    means in communication with said interior for removing a sample of the fluid from said vessel;
    means in communication with said interior for draining the fluid from said vessel; and
    means for sensing temperatures of the fluid within the vessel; and
    means for correlating said sensed temperatures with said flow rates.

2. The apparatus of claim 1, further including means connected to said sensing means for recording said temperatures as a function of time.

3. The apparatus of claim 2, wherein said temperature sensing means comprises a thermometer carried in said interior of said vessel.

4. The apparatus of claim 2, further including an internal temperature sensor for detecting ambient temperatures inside said vessel.

5. The apparatus of claim 4, wherein said recording means comprises a microprocessor coupled to said temperature sensing means, said microprocessor having a memory.

6. The apparatus of claim 5, wherein said internal reference temperature sensor is coupled to said microprocessor.

7. The apparatus of claim 6, wherein said microprocessor includes means for compensating for said ambient temperatures in recording said fluid temperatures.

8. The apparatus of claim 5, including means coupled to said microprocessor for displaying said fluid temperatures as a function of time.

9. The apparatus of claim 1, wherein:
    said first dielectric comprises at least a portion of said wall;
    said second dielectric comprises an air space; and
    said second electrode is carried within said interior and adjacent said air space, such that as the fluid is collected in said vessel, the fluid displaces air in said air space, thereby varying the capacitance of said capacitor.

10. The apparatus of claim 9, wherein said flow rate determining means includes:
    a capacitance circuit connected to said variable capacitor and including a first point and a second point, wherein said first point and said second point have a predetermined potential difference when said vessel contains no fluid and, as the fluid is collected in said vessel, having varying potential differences which vary as a function of said capacitance value;
    means connected to said first and second points for detecting said predetermined potential difference and said varying potential differences between said first and second points at predetermined time intervals;
    means connected to said detecting means for converting said predetermined potential difference and said varying potential differences into numerical values related to said flow rates.

11. The apparatus of claim 10, wherein said predetermined potential difference is nonzero.

12. An apparatus for measuring temperatures and flow rates of a fluid, comprising:
    a vessel including a wall defining an interior and an exterior, said interior for collecting an amount of the fluid;
    a first electrode comprising a first electrical conductor disposed adjacent said wall at said exterior;
    a second electrode carried in said interior of said vessel;
    a first dielectric disposed adjacent said first electrode for insulating said first electrode from said second electrode and from said fluid;
    a second dielectric disposed adjacent said second electrode and in communication with said vessel interior, such that said first and second electrodes and said first and second dielectrics together comprise a variable capacitor with a capacitance value which varies with said amount of fluid;
    means connected to said variable capacitor for determining the flow rates of the fluid as a function of said capacitance value and for providing an output reflecting said flow rates;
    means for displaying said flow rates;
    means in communication with said interior for removing a sample of the fluid from said vessel;
    means in communication with said interior for draining the fluid from said vessel;
    means for sensing temperatures of the fluid within the vessel, wherein said temperature sensing means comprises an infrared optical sensor directed at a portion of said vessel; and
    means connected to said sensing means for recording said temperatures as a function of time.

13. The apparatus of claim 12, wherein said portion of said vessel is on an exterior thereof.

14. The apparatus of claim 13, wherein said exterior portion is thinner relative to other portions of said vessel.

15. The apparatus of claim 14, wherein said exterior portion is dark in color.

16. The apparatus of claim 15, wherein said exterior portion comprises a hole in said vessel covered in a sealed fashion by black tape.

17. The apparatus of claim 12, wherein said portion is on said interior of said vessel.

18. An apparatus for measuring temperatures and flow rates of a fluid, comprising:
- a vessel including a wall defining an interior and an exterior, said interior for collecting an amount of the fluid;
- a first electrode comprising a first electrical conductor disposed adjacent said wall at said exterior;
- a second electrode carried in said interior of said vessel, wherein said first electrode comprises a plate conforming to an exterior shape of said vessel, and said second electrode comprises a wire vertically disposed in the interior of said vessel and near said wall substantially opposite said plate;
- a first dielectric disposed adjacent said first electrode for insulating said first electrode from said second electrode and from said fluid, wherein said first dielectric comprises at least a portion of said wall;
- a second dielectric disposed adjacent said second electrode and in communication with said vessel interior, wherein said second dielectric comprises an air space, such that said first and second electrodes and said first and second dielectrics together comprise a variable capacitor with a capacitance value which varies with said amount of fluid, wherein said second electrode is carried within said interior and adjacent said air space, such that as the fluid is collected in said vessel, the fluid displaces air in said air space, thereby varying the capacitance of said capacitor;
- means connected to said variable capacitor for determining the flow rates of the fluid as a function of said capacitance value and for providing an output reflecting said flow rates;
- means for displaying said flow rates;
- means in communication with said interior for removing a sample of the fluid from said vessel;
- means in communication with said interior for draining the fluid from said vessel; and
- means for sensing temperatures of the fluid within the vessel.

19. The apparatus of claim 18, wherein said first electrode and second electrode, respectively, comprise strips of conductor tape.

20. The apparatus of claim 19, wherein said draining means includes:
- an aperture for providing fluid communication between said interior and said exterior of said vessel;
- a plug disposed adjacent said aperture for preventing the fluid from passing through said aperture; and
- means for removing the plug from a point remote from said interior of said vessel.

21. The apparatus of claim 20, wherein said removing means includes an elongate flexible means for pulling said plug, said pulling means having one end attached to said plug and having another end extending to said exterior of said vessel.

22. The apparatus of claim 21, wherein said vessel, said first dielectric, said removing means, said draining means, and said second electrode comprise a single unit for disposal of said unit when the flow rates of the fluid have been measured.

23. An apparatus for measuring temperatures and flow rates of a fluid, comprising:
- a vessel including a wall defining an interior and an exterior, said interior for collecting an amount of the fluid;
- a first electrode comprising a first electrical conductor disposed adjacent said wall at said exterior;
- a second electrode carried in said interior of said vessel;
- a first dielectric disposed adjacent said first electrode for insulating said first electrode from said second electrode and from said fluid, wherein said first dielectric comprises at least a portion of said wall;
- a second dielectric disposed adjacent said second electrode and in communication with said vessel interior, wherein said second dielectric comprises an air space, such that said first and second electrodes and said first and second dielectrics together comprise a variable capacitor with a capacitance value which varies with said amount of fluid, wherein said second electrode is carried within said interior and adjacent said air space, such that as the fluid is collected in said vessel, the fluid displaces air in said air space, thereby varying the capacitance of said capacitor;
- means connected to said variable capacitor for determining the flow rates of the fluid as a function of said capacitance value and for providing an output reflecting said flow rates;
- means for displaying said flow rates; and
- means in communication with said interior for removing a sample of the fluid from said vessel, wherein said removing means includes:
  - a tube extending into the said interior of said vessel, said tube including a closure;
  - means for opening said tube; and
  - means for drawing a sample of the fluid through said tube for transfer to a container separate from the vessel; the apparatus further including:
- means in communication with said interior for draining the fluid from said vessel; and
- means for sensing temperatures of the fluid within the vessel.

24. An apparatus for measuring temperatures and flow rates of a fluid, comprising:
- a vessel including a wall defining an interior and an exterior, said interior for collecting an amount of the fluid;
- a first electrode comprising a first electrical conductor disposed adjacent said wall at said exterior;
- a second electrode carried in said interior of said vessel;
- a first dielectric disposed adjacent said first electrode for insulating said first electrode from said second electrode and from said fluid, wherein said first dielectric comprises at least a portion of said wall;
- a second dielectric disposed adjacent said second electrode and in communication with said vessel interior, wherein said second dielectric comprises an air space, such that said first and second electrodes and said first and second dielectrics together comprise a variable capacitor with a capacitance value which varies with said amount of fluid, wherein said second electrode is carried within said interior and adjacent said air space, such that as the fluid is collected in said vessel, the fluid displaces air in said air space, thereby varying the capacitance of said capacitor; and means connected to said variable capacitor for determining the flow rates of the fluid as a function of said capacitance value and for providing an output reflecting said flow rates, wherein said flow rate determining means includes:
- a capacitance circuit connected to said variable capacitor and including a first point and a second point, wherein said first point and said second point have a predetermined potential difference when said vessel contains no fluid and, as the fluid is collected in said vessel, have varying potential differences which vary as a function of said capacitance value;
- means connected to said first and second points for detecting said predetermined potential difference and said varying potential differences between said first and second points at predetermined time intervals;
- means connected to said detecting means for converting said predetermined potential difference and said varying potential differences into numerical values related to said plow rates, wherein said converting means is also for converting said predetermined potential difference and said varying potential differences into numerical values representing initial and final volume readings of said vessel; and
- a microprocessor for generating retrospective averages of said flow rates for a first block of said predetermined time intervals, for generating prospective averages of said flow rates for a second block of said predetermined time interval, where said second block has an overlap with said first block, and for generating combined averages for said overlap, said combined averages being derived from said retrospective averages and said prospective averages, with one said combined average relating to each of said predetermined intervals in said overlap, and for substituting said retrospective averages, said prospective averages, and said combined averages for said flow readings in said memory; the apparatus further including:

means for displaying said flow rates;

means in communication with said interior for removing a sample of the fluid from said vessel;

means in communication with said interior for draining the fluid from said vessel; and means for sensing temperatures of the fluid within the vessel.

* * * * *